United States Patent
Bachinger et al.

(10) Patent No.: US 9,315,561 B2
(45) Date of Patent: Apr. 19, 2016

(54) COMPOSITIONS COMPRISING THE NC2 DOMAIN OF COLLAGEN IX AND METHODS OF USING SAME

(71) Applicants: Hans Peter Bachinger, Beaverton, OR (US); Sergey P. Budko, Hillsboro, OR (US)

(72) Inventors: Hans Peter Bachinger, Beaverton, OR (US); Sergey P. Budko, Hillsboro, OR (US)

(73) Assignee: SHRINERS HOSPITAL FOR CHILDREN, Tampa, FL (US)

(*) Notice: Subject to any disclaimer, the term of this patent is extended or adjusted under 35 U.S.C. 154(b) by 0 days.

(21) Appl. No.: 13/684,310

(22) Filed: Nov. 23, 2012

(65) Prior Publication Data
US 2013/0157257 A1    Jun. 20, 2013

Related U.S. Application Data

(63) Continuation of application No. PCT/US2011/037923, filed on May 25, 2011.

(60) Provisional application No. 61/348,735, filed on May 26, 2010.

(51) Int. Cl.
*C07K 14/78* (2006.01)
*A61K 38/16* (2006.01)
*A61K 38/39* (2006.01)

(52) U.S. Cl.
CPC ............... *C07K 14/78* (2013.01); *A61K 38/16* (2013.01); *A61K 38/39* (2013.01); *C07K 2319/00* (2013.01); *C07K 2319/01* (2013.01)

(58) Field of Classification Search
CPC .............. A61K 2300/00; A61K 38/39; A61K 38/1841; A61K 31/726; A61K 35/28; A61K 38/00; A61K 38/1709; A61K 8/65; A61K 49/0056; A61L 27/3633; A61L 27/24; A61L 31/16; C07K 14/78; C07K 2319/00; C07K 2319/01; C07K 14/47

See application file for complete search history.

(56) References Cited

U.S. PATENT DOCUMENTS

| 5,925,736 A | * | 7/1999 | Neff et al. ................. 530/356 |
| 2005/0202537 A1 | * | 9/2005 | Liang .......................... 435/69.7 |

FOREIGN PATENT DOCUMENTS

| IL | WO 2007/026362 A2 | * | 3/2007 | ............. A61K 48/00 |
| WO | 9717988 | | 5/1997 | |
| WO | WO 97/17988 | * | 5/1997 | ............. A61K 38/17 |
| WO | WO 2005/113794 A1 | * | 12/2005 | ............... C12Q 1/02 |

OTHER PUBLICATIONS

Sato et al. Type XXVI collagen, a new member of the collagen family, is specifically expressed in the testis and ovary. J Biol Chem. Oct. 4, 2002;277(40):37678-84.*

(Continued)

Primary Examiner — Karlheinz R Skowronek
Assistant Examiner — Jia-Hai Lee
(74) Attorney, Agent, or Firm — Baker Botts L.L.P.

(57) ABSTRACT

The present invention relates to the newly identified timerization initiating and stagger determining capacity of the NC2 domain of collagen IX. The invention further relates to a hexavalent molecular building block wherein the linkage of additional moieties to the amino and carboxyl terminals of monomers comprising the NC2 domain of collagen IX promotes the directed association of those moieties via the trimerization initiating and stagger determining capacity of the NC2 domain of collagen IX.

11 Claims, 9 Drawing Sheets

(56) References Cited

OTHER PUBLICATIONS

Diab et al. Collagen type IX from human cartilage: a structural profile of intermolecular cross-linking sites. Biochem J. Feb. 15, 1996;314 (Pt 1):327-32.*

Boudko et al. Trimerization and triple helix stabilization of the collagen XIX NC2 domain. J Biol Chem. Dec. 5, 2008;283(49):34345-51.*

Olson BR. Collagen IX. Int. J. Biochem. Cell Biol. 1997; 29: 5.*

Archer, et al., "An alternative 3D NMR technique for correlating backbone $^{15}N$ with side chain Hβ resonances in larger proteins", *Journal of Magnetic Resonance*, 95:636-641 (1991).

Asamura, et al., "Type IX collagen is crucial for normal hearing", *Neuroscience*, 132:493-500 (2005).

Berision, et al., "Crystal structure of the collagen triple helix model [(Pro-Pro-Gly)]$_{10}$]$_3$", *Protein Science*, 11:262-270 (2002).

Boudko, et al., "Structure formation in the C terminus of type III collagen guides disulfide cross-linking", *JMB*, 335:1289-1297 (2004).

Boudko, et al., "Trimerization and triple helix stabilization of the collagen XIX NC2 domain", *The Journal of Biological Chemistry*, 283(49):34345-34351 (2008).

Boudko, et al., "Crystal structure of human type III collagen Gly$^{991}$-Gly$^{1032}$ cystine knot-containing peptide shows both 7/2 and 10/3 triple helical symmetries", *The Journal of Biological Chemistry*, 283(47):32580-32589 (2008).

Boyd, et al., "Early-Onset degeneration of the intervertebral disc and vertebral end plate in mice deficient in type IX collagen", *Arthritis & Rheumatism*, 58(1):164-171 (2008).

Bruckner, et al., "The structure of human collagen type IX and its organization in fetal and infant cartilage fibrils", *The Journal of Biological Chemistry*, 263(32):16911-16917 (1988).

Brünger, et al., "Crystallography & NMR System: A new software suite for macromolecular structure determination", *Acta Cryst.*, D54:905-921 (1998).

Burrage, et al., "Matrix metalloproteinases: Role in arthritis", *Frontiers in Bioscience*, 11:529-543 (2006).

Carter, et al., "Genetic and orthopedic aspects of collagen disorders", *Current Opinion in Pediatrics*, 21:46-54 (2009).

Case, et al., "The amber biomolecular simulation programs", *J. Comput. Chem.*, 26:1668-1688 (2005).

Delaglio, et al., "NMRPipe: A multidimensional spectral processing system based on UNIX pipes", *Journal of Biomolecular NMR*, 6:277-293 (1995).

Delano, "The PyMOL molecular graphics system", Delano Scientific, San Carlos, California (2002) (2 pages), http://www.pymol.org [Retrieved on Apr. 2, 2013].

Diab, "The role of the type IX collagen in osteoarthritis and rheumatoid arthritis", *Orthopedic Review*, 22:165-170 (1993).

DiCesare, et al., "Cartilage oligomeric matrix protein (COMP) is an abundant component of tendon", *FEBS Letters*, 354:237-240 (1994).

Eyre, et al., "Collagen structure and cartilage matrix integrity", *The Journal of Rheumatology*, 22(Suppl. 43):82-88 (1995).

Fässler, et al., "Mice lacking α1(IX) collagen develop noninflammatory degenerative joint disease", *PNAS*, 91:5070-5074 (1994).

Fresquet, et al., "Structural and functional characterization of recombinant matrilin-3 A-domain and implications for human genetic bone diseases", *The Journal of Biological Chemistry*, 282(48):34634-34643 (2007).

Goddard, et al., "Sparky—NMR assignment and integration software", Sparky 3, version 3.115, University of California, San Francisco, 3 pages [Retrieved on Apr. 2, 2013] (2008).

Hedbom, et al., "Cartilage matrix proteins", *The Journal of Biological Chemistry*, 267(9):6132-6136 (1992).

Holden, et al., "Cartilage oligomeric matrix protein interacts with type IX collagen, and disruptions to these interactions identify a pathogenetic mechanism in a bone dysplasia family", *The Journal of Biological Chemistry*, 276(8):6046-6055 (2001).

Jäälinoja, et al., "Trimerization of collagen IX α-chains does not require the presence of the COL1 and NC1 domains", *Biochem.*, 409:545-554 (2008).

Jäälinoja, et al., "Serum antibodies against intact human collagen IX are elevated at onset of rheumatoid arthritis but are not related to development of erosions", *The Journal of Rheumatology*, 35(5):745-751 (2008).

Jones, et al., "Improved methods for building protein models in electron density maps and the location of errors in these models", *Acta Crystallographica*, A47:110-119 (1991).

Kammerer, et al., "Tenascin-C hexabrachion assembly is a sequential two-step process initiated by coiled-coil α-helices", *The Journal of Biological Chemistry*, 273(17):10602-10608 (1998).

Labourdette, et al., "Analysis of the role of the COLI domain and its adjacent cysteine-containing sequence in the chain assembly of type IX collagen", *FEBS Letters*, 320(3):211-214 (1993).

Laskowski, et al., "Computer Programs", *J. Appl. Cryst.*, 26:283-291 (1993).

Leppänen, et al., "Crystal structure if the N-terminal NC4 domain of collagen IX, a zinc binding member of the laminin-neurexin-sex hormone binding globulin (LNS) domain family", *The Journal of Biological Chemistry*, 282(32):23219-23230 (2007).

Lesage, et al., "Trimeric assembly and three-dimensional structure model of the FACIT collagen COL1-NC1 junction from CD and NMR analysis", *Biochemistry*, 35:9647-9660 (1996).

Li, et al., "Two-dimensional NMR assignments and conformation of (Pro-Hyp-Gly)$_{10}$ and a designed collagen triple-helical peptide", *Biochemistry*, 32:7377-7387 (1993).

Mazzorana, et al., "Mechanisms of Collagen trimer formation", *The Journal of Biological Chemistry*, 268(5):3029-3032 (1993).

Mazzorana, et al., "Collagenous sequence governs the trimeric assembly of collagen XII", *The Journal of Biological Chemistry*, 276(30):27989-27998 (2001).

McAlindent, et al., "α-Helical coiled-coil oligomerization domains are almost ubiquitous in the collagen superfamily", *The Journal of Biological Chemistry*, 278(43):42200-42207 (2003).

Mechling, et al., "Type IX collagen NC1 domain peptides can trimerize in vitro without forming a triple helix", *The Journal of Biological Chemistry*, 271(23):13781-13785 (1996).

Mörgelin, et al., "The cartilage proteoglycan aggregate: assembly through combined protein-carbohydrate and protein-protein interactions", *Biophysical Chemistry*, 50:113-128 (1994).

Muhandiram, et al., "An enhanced-sensitivity pure absorption gradients 4D $^{15}N$, $^{13}C$-edited NOESY experiment", *Journal of Biomolecular*, 3:463-470 (1993).

Munakata, et al., "Interaction between collagens and glycosaminoglycans investigated using a surface plasmon resonance biosensor", *Glycobiology*, 9(10):1023-1027 (1999).

Myllyharju, et al., "Collagens, modifying enzymes and their mutations in humans, flies and worms", *TRENDS in Genetics*, 20(1):33-43 (2004).

Okada, et al., "Degradation of type IX collagen by matrix metalloproteinase 3 (stromelysin) from human rheumatoid synovial cells", *FEBS Letters*, 244(2):473-476 (1989).

Okuyama, et al., "Helical twists of collagen model peptides", *Biopolymers (Pept Sci)*, 84:421-432 (2006).

Paassilta, et al., "Complete sequence of the 23-kilobase human COL9A3 gene", *The Journal of Biological Chemistry*, 274(32):22469-22475 (1999).

Park, et al., "A new set of ,olecular mechanics parameters for hydroxyproline ans its use in molecular dynamics simulations of collagen-like peptides", *J. Comput. Chem.*, 26:1612-1616 (2005).

Pihlajamaa, et al., "Characterization of recombinant human type IX collagen", *The Journal of Biological Chemistry*, 274(32):22464-22468 (1999).

Pihlajamaa, et al., "Characterization if recombinant amino-terminal NC4 domain of human collagen IX", *The Journal of Biological Chemistry*, 279(23):24265-24273 (2004).

Powers, et al., "The high-resolution, three-dimensional solution structure of human interleukin-4 determined by multidimensional heteronuclear magnetic resonance spectroscopy", *Biochemistry*, 32:6744-6762 (1993).

(56) References Cited

OTHER PUBLICATIONS

Ricard-Blum, et al., "The collagen superfamily: from the extracellular matrix to the cell membrane", *Pathologic Biologie*, 53:430-442 (2005).

Rosenberg, et al., "Cartilage oligomeric matrix protein shows high affinity zinc-dependent interaction with triple helical collagen", *The Journal of Biological Chemistry*, 273(32):20397-20403 (1998).

Rowley, et al., "The role of collagen antibodies in mediating arthritis", *Mod. Rheumatol.*, 18:429-441 (2008).

Sugeta, et al., "General method for calculating helical parameters of polymer chains from bond lengths, bond angles, and internal-rotation angles", *Biopolymers*, 5:673-679 (1967).

Terwilliger, et al., "Automated MAD and MIR structure solution", *Acta Crystallographica Section D*, D55:849-861 (1999).

Thur, et al., "Mutations in cartilage oligomeric matrix protein causing pseudoachondroplasia and multiple epiphyseal dysplasia affect binding of calcium and collagen I, II, and IX", *The Journal of Biological Chemistry*, 276(9):6083-6092 (2001).

van der Rest, et al., "Type IX collagen proteoglycan from cartilage is covalently cross-linked to type II collagen", *The Journal of Biological Chemistry*, 263(4):1615-1618 (1988).

Vaughan, et al., "D-Periodic distribution of collagen type IX along cartilage fibrils", *The Journal of Cell Biology*, 106:991-997 (1988).

Vranken, et al., "The CCPN data model for NMR spectroscopy: Development of a software pipeline", *PROTEINS: Structure, Function, and Bioinformatics*, 59:687-696 (2005).

Vuister, et al., "Quantitive $J$ Correlation: A new approach for measuring homonuclear three-bond $J(H^N H^\alpha)$ coupling constants in $^{15}$N-enriched proteins", *J. Am. Chem. Soc.*, 115:7772-7777 (1993).

Wu, et al., "Sites of stromelysin cleavage in collagen types II, IX, X, and XI of cartilage", *The Journal of Biological Chemistry*, 266(9):5625-5628 (1991).

\* cited by examiner

SEQUENCE LISTING

<160> NUMBER OF SEQ ID NOS: 24

<210> SEQ ID NO 1
<211> LENGTH: 921
<212> TYPE: PRT
<213> ORGANISM: Homo sapiens

<400> SEQUENCE: 1

Met Lys Thr Cys Trp Lys Ile Pro Val Phe Phe Phe Val Cys Ser Phe

```
1               5                   10                  15
Leu Glu Pro Trp Ala Ser Ala Ala Val Lys Arg Arg Pro Arg Phe Pro
                20                  25                  30
Val Asn Ser Asn Ser Asn Gly Gly Asn Glu Leu Cys Pro Lys Ile Arg
                35                  40                  45
Ile Gly Gln Asp Asp Leu Pro Gly Phe Asp Leu Ile Ser Gln Phe Gln
                50                  55                  60
Val Asp Lys Ala Ala Ser Arg Arg Ala Ile Gln Arg Val Val Gly Ser
 65                 70                  75                  80
Ala Thr Leu Gln Val Ala Tyr Lys Leu Gly Asn Asn Val Asp Phe Arg
                85                  90                  95
Ile Pro Thr Arg Asn Leu Tyr Pro Ser Gly Leu Pro Glu Glu Tyr Ser
                100                 105                 110
Phe Leu Thr Thr Phe Arg Met Thr Gly Ser Thr Leu Lys Lys Asn Trp
                115                 120                 125
Asn Ile Trp Gln Ile Gln Asp Ser Ser Gly Lys Glu Gln Val Gly Ile
                130                 135                 140
Lys Ile Asn Gly Gln Thr Gln Ser Val Val Phe Ser Tyr Lys Gly Leu
145                 150                 155                 160
Asp Gly Ser Leu Gln Thr Ala Ala Phe Ser Asn Leu Ser Ser Leu Phe
                165                 170                 175
Asp Ser Gln Trp His Lys Ile Met Ile Gly Val Glu Arg Ser Ser Ala
                180                 185                 190
Thr Leu Phe Val Asp Cys Asn Arg Ile Glu Ser Leu Pro Ile Lys Pro
                195                 200                 205
Arg Gly Pro Ile Asp Ile Asp Gly Phe Ala Val Leu Gly Lys Leu Ala
                210                 215                 220
Asp Asn Pro Gln Val Ser Val Pro Phe Glu Leu Gln Trp Met Leu Ile
225                 230                 235                 240
His Cys Asp Pro Leu Arg Pro Arg Arg Glu Thr Cys His Glu Leu Pro
                245                 250                 255
Ala Arg Ile Thr Pro Ser Gln Thr Thr Asp Glu Arg Gly Pro Pro Gly
                260                 265                 270
Glu Gln Gly Pro Pro Gly Pro Pro Gly Pro Pro Gly Val Pro Gly Ile
                275                 280                 285
Asp Gly Ile Asp Gly Asp Arg Gly Pro Lys Gly Pro Pro Gly Pro Pro
                290                 295                 300
Gly Pro Ala Gly Glu Pro Gly Lys Pro Gly Ala Pro Gly Lys Pro Gly
305                 310                 315                 320
Thr Pro Gly Ala Asp Gly Leu Thr Gly Pro Asp Gly Ser Pro Gly Ser
                325                 330                 335
Ile Gly Ser Lys Gly Gln Lys Gly Glu Pro Gly Val Pro Gly Ser Arg
                340                 345                 350
Gly Phe Pro Gly Arg Gly Ile Pro Gly Pro Gly Pro Gly Thr
                355                 360                 365
Ala Gly Leu Pro Gly Glu Leu Gly Arg Val Gly Pro Val Gly Asp Pro
                370                 375                 380
Gly Arg Arg Gly Pro Pro Gly Pro Gly Pro Pro Gly Pro Arg Gly
385                 390                 395                 400
Thr Ile Gly Phe His Asp Gly Asp Pro Leu Cys Pro Asn Ala Cys Pro
                405                 410                 415
Pro Gly Arg Ser Gly Tyr Pro Gly Leu Pro Gly Met Arg Gly His Lys
                420                 425                 430
```

```
Gly Ala Lys Gly Glu Ile Gly Glu Pro Gly Arg Gln Gly His Lys Gly
            435                 440                 445

Glu Glu Gly Asp Gln Gly Leu Gly Glu Val Gly Ala Gln Gly Pro
        450                 455                 460

Pro Gly Ala Gln Gly Leu Arg Gly Ile Thr Gly Ile Val Gly Asp Lys
465                 470                 475                 480

Gly Glu Lys Gly Ala Arg Gly Leu Asp Gly Glu Pro Gly Pro Gln Gly
                485                 490                 495

Leu Pro Gly Ala Pro Gly Asp Gln Gly Gln Arg Gly Pro Pro Gly Glu
            500                 505                 510

Ala Gly Pro Lys Gly Asp Arg Gly Ala Glu Gly Ala Arg Gly Ile Pro
        515                 520                 525

Gly Leu Pro Gly Pro Lys Gly Asp Thr Gly Leu Pro Gly Val Asp Gly
    530                 535                 540

Arg Asp Gly Ile Pro Gly Met Pro Gly Thr Lys Gly Glu Pro Gly Lys
545                 550                 555                 560

Pro Gly Pro Pro Gly Asp Ala Gly Leu Gln Gly Leu Pro Gly Val Pro
                565                 570                 575

Gly Ile Pro Gly Ala Lys Gly Val Ala Gly Glu Lys Gly Ser Thr Gly
            580                 585                 590

Ala Pro Gly Lys Pro Gly Gln Met Gly Asn Ser Gly Lys Pro Gly Gln
        595                 600                 605

Gln Gly Pro Pro Gly Glu Val Gly Pro Arg Gly Pro Gln Gly Leu Pro
    610                 615                 620

Gly Ser Arg Gly Glu Leu Gly Pro Val Gly Ser Pro Gly Leu Pro Gly
625                 630                 635                 640

Lys Leu Gly Ser Leu Gly Ser Pro Gly Leu Pro Gly Leu Pro Gly Pro
                645                 650                 655

Pro Gly Leu Pro Gly Met Lys Gly Asp Arg Gly Val Val Gly Glu Pro
            660                 665                 670

Gly Pro Lys Gly Glu Gln Gly Ala Ser Gly Glu Gln Gly Glu Ala Gly
        675                 680                 685

Glu Arg Gly Glu Leu Gly Asp Ile Gly Leu Pro Gly Pro Lys Gly Ser
    690                 695                 700

Ala Gly Asn Pro Gly Glu Pro Gly Leu Arg Gly Pro Glu Gly Ser Arg
705                 710                 715                 720

Gly Leu Pro Gly Val Glu Gly Pro Arg Gly Pro Pro Gly Pro Arg Gly
                725                 730                 735

Val Gln Gly Glu Gln Gly Ala Thr Gly Leu Pro Gly Val Gln Gly Pro
            740                 745                 750

Pro Gly Arg Ala Pro Thr Asp Gln His Ile Lys Gln Val Cys Met Arg
        755                 760                 765

Val Ile Gln Glu His Phe Ala Glu Met Ala Ala Ser Leu Lys Arg Pro
    770                 775                 780

Asp Ser Gly Ala Thr Gly Leu Pro Gly Arg Pro Gly Pro Pro Gly Pro
785                 790                 795                 800

Pro Gly Pro Pro Gly Glu Asn Gly Phe Pro Gly Gln Met Gly Ile Arg
                805                 810                 815

Gly Leu Pro Gly Ile Lys Gly Pro Pro Gly Ala Leu Gly Leu Arg Gly
            820                 825                 830

Pro Lys Gly Asp Leu Gly Glu Lys Gly Glu Arg Gly Pro Pro Gly Arg
        835                 840                 845
```

-continued

```
Gly Pro Asn Gly Leu Pro Gly Ala Ile Gly Leu Pro Gly Asp Pro Gly
    850                 855                 860

Pro Ala Ser Tyr Gly Arg Asn Gly Arg Asp Gly Glu Arg Gly Pro Pro
865                 870                 875                 880

Gly Val Ala Gly Ile Pro Gly Val Pro Gly Pro Pro Gly Pro Pro Gly
                885                 890                 895

Leu Pro Gly Phe Cys Glu Pro Ala Ser Cys Thr Met Gln Ala Gly Gln
            900                 905                 910

Arg Ala Phe Asn Lys Gly Pro Asp Pro
        915                 920

<210> SEQ ID NO 2
<211> LENGTH: 689
<212> TYPE: PRT
<213> ORGANISM: Homo sapiens

<400> SEQUENCE: 2

Met Ala Ala Thr Ala Ser Pro Arg Ser Leu Leu Val Leu Leu Leu Gln
1               5                   10                  15

Val Val Val Leu Ala Leu Ala Gln Ile Arg Gly Pro Pro Gly Glu Arg
            20                  25                  30

Gly Pro Pro Gly Pro Pro Gly Pro Pro Gly Val Pro Gly Ser Asp Gly
        35                  40                  45

Ile Asp Gly Asp Asn Gly Pro Pro Gly Lys Ala Gly Pro Pro Gly Pro
50                  55                  60

Lys Gly Glu Pro Gly Lys Ala Gly Pro Asp Gly Pro Asp Gly Lys Pro
65                  70                  75                  80

Gly Ile Asp Gly Leu Thr Gly Ala Lys Gly Glu Pro Gly Pro Met Gly
                85                  90                  95

Ile Pro Gly Val Lys Gly Gln Pro Gly Leu Pro Gly Pro Pro Gly Leu
            100                 105                 110

Pro Gly Pro Gly Phe Ala Gly Pro Pro Gly Pro Pro Gly Pro Val Gly
        115                 120                 125

Leu Pro Gly Glu Ile Gly Ile Arg Gly Pro Lys Gly Asp Pro Gly Pro
130                 135                 140

Asp Gly Pro Ser Gly Pro Pro Gly Pro Pro Gly Lys Pro Gly Arg Pro
145                 150                 155                 160

Gly Thr Ile Gln Gly Leu Glu Gly Ser Ala Asp Phe Leu Cys Pro Thr
                165                 170                 175

Asn Cys Pro Pro Gly Met Lys Gly Pro Pro Gly Leu Gln Gly Val Lys
            180                 185                 190

Gly His Ala Gly Lys Arg Gly Ile Leu Gly Asp Pro Gly His Gln Gly
        195                 200                 205

Lys Pro Gly Pro Lys Gly Asp Val Gly Ala Ser Gly Glu Gln Gly Ile
    210                 215                 220

Pro Gly Pro Pro Gly Pro Gln Gly Ile Arg Gly Tyr Pro Gly Met Ala
225                 230                 235                 240

Gly Pro Lys Gly Glu Thr Gly Pro His Gly Tyr Lys Gly Met Val Gly
                245                 250                 255

Ala Ile Gly Ala Thr Gly Pro Pro Gly Glu Glu Gly Arg Gly Pro Pro
            260                 265                 270

Pro Gly Arg Ala Gly Glu Lys Gly Asp Glu Gly Ser Pro Gly Ile Arg
        275                 280                 285

Gly Pro Gln Gly Ile Thr Gly Pro Lys Gly Ala Thr Gly Pro Pro Gly
    290                 295                 300
```

Ile Asn Gly Lys Asp Gly Thr Pro Thr Pro Gly Met Lys Gly Ser
305                 310                 315                 320

Ala Gly Gln Ala Gly Gln Pro Gly Ser Pro Gly His Gln Gly Leu Ala
            325                 330                 335

Gly Val Pro Gly Gln Pro Gly Thr Lys Gly Pro Gly Asp Gln Gly
            340                 345                 350

Glu Pro Gly Pro Gln Gly Leu Pro Gly Phe Ser Gly Pro Pro Gly Lys
            355                 360                 365

Glu Gly Glu Pro Gly Pro Arg Gly Glu Ile Gly Pro Gln Gly Ile Met
        370                 375                 380

Gly Gln Lys Gly Asp Gln Gly Glu Arg Gly Pro Val Gly Gln Pro Gly
385                 390                 395                 400

Pro Gln Gly Arg Gln Gly Pro Lys Gly Glu Gln Gly Pro Pro Gly Ile
            405                 410                 415

Pro Gly Pro Gln Gly Leu Pro Gly Val Lys Gly Asp Lys Gly Ser Pro
            420                 425                 430

Gly Lys Thr Gly Pro Arg Gly Lys Val Gly Asp Pro Gly Val Ala Gly
        435                 440                 445

Leu Pro Gly Glu Lys Gly Glu Lys Gly Glu Ser Gly Glu Pro Gly Pro
    450                 455                 460

Lys Gly Gln Gln Gly Val Arg Gly Glu Pro Gly Tyr Pro Gly Pro Ser
465                 470                 475                 480

Gly Asp Ala Gly Ala Pro Gly Val Gln Gly Tyr Pro Gly Pro Pro Gly
            485                 490                 495

Pro Arg Gly Leu Ala Gly Asn Arg Gly Val Pro Gly Pro Gly Pro Gly Arg
            500                 505                 510

Gln Gly Val Glu Gly Arg Asp Ala Thr Asp Gln His Ile Val Asp Val
        515                 520                 525

Ala Leu Lys Met Leu Gln Glu Gln Leu Ala Glu Val Ala Val Ser Ala
    530                 535                 540

Lys Arg Glu Ala Leu Gly Ala Val Gly Met Met Gly Pro Pro Gly Pro
545                 550                 555                 560

Pro Gly Pro Pro Gly Tyr Pro Gly Lys Gln Gly Pro His Gly His Pro
            565                 570                 575

Gly Pro Arg Gly Val Pro Gly Ile Val Gly Ala Val Gly Gln Ile Gly
            580                 585                 590

Asn Thr Gly Pro Lys Gly Lys Arg Gly Glu Lys Gly Asp Pro Gly Glu
        595                 600                 605

Val Gly Arg Gly His Pro Gly Met Pro Gly Pro Gly Ile Pro Gly
    610                 615                 620

Leu Pro Gly Arg Pro Gly Gln Ala Ile Asn Gly Lys Asp Gly Asp Arg
625                 630                 635                 640

Gly Ser Pro Gly Ala Pro Gly Glu Ala Gly Arg Pro Gly Leu Pro Gly
            645                 650                 655

Pro Val Gly Leu Pro Gly Phe Cys Glu Pro Ala Ala Cys Leu Gly Ala
            660                 665                 670

Ser Ala Tyr Ala Ser Ala Arg Leu Thr Glu Pro Gly Ser Ile Lys Gly
        675                 680                 685

Pro

<210> SEQ ID NO 3
<211> LENGTH: 684
<212> TYPE: PRT

<213> ORGANISM: Homo sapiens

<400> SEQUENCE: 3

```
Met Ala Gly Pro Arg Ala Cys Ala Pro Leu Leu Leu Leu Leu Leu Leu
1               5                   10                  15
Gly Glu Leu Leu Ala Ala Gly Ala Gln Arg Val Gly Leu Pro Gly
            20                  25                  30
Pro Pro Gly Pro Pro Gly Pro Pro Gly Lys Pro Gly Gln Asp Gly Ile
            35                  40                  45
Asp Gly Glu Ala Gly Pro Pro Gly Leu Pro Gly Pro Pro Gly Pro Lys
        50                  55                  60
Gly Ala Pro Gly Lys Pro Gly Lys Pro Gly Glu Ala Gly Leu Pro Gly
65                  70                  75                  80
Leu Pro Gly Val Asp Gly Leu Thr Gly Arg Asp Gly Pro Pro Gly Pro
                85                  90                  95
Lys Gly Ala Pro Gly Glu Arg Gly Ser Leu Gly Pro Pro Gly Pro Pro
            100                 105                 110
Gly Leu Gly Gly Lys Gly Leu Pro Gly Pro Pro Gly Glu Ala Gly Val
            115                 120                 125
Ser Gly Pro Pro Gly Gly Ile Gly Leu Arg Gly Pro Pro Gly Pro Ser
    130                 135                 140
Gly Leu Pro Gly Leu Pro Gly Pro Pro Gly Pro Pro Gly Pro Pro Gly
145                 150                 155                 160
His Pro Gly Val Leu Pro Glu Gly Ala Thr Asp Leu Gln Cys Pro Ser
                165                 170                 175
Ile Cys Pro Pro Gly Pro Pro Gly Pro Pro Gly Met Pro Gly Phe Lys
            180                 185                 190
Gly Pro Thr Gly Tyr Lys Gly Glu Gln Gly Glu Val Gly Lys Asp Gly
            195                 200                 205
Glu Lys Gly Asp Pro Gly Pro Pro Gly Pro Ala Gly Leu Pro Gly Ser
    210                 215                 220
Val Gly Leu Gln Gly Pro Arg Gly Leu Arg Gly Leu Pro Gly Pro Leu
225                 230                 235                 240
Gly Pro Pro Gly Asp Arg Gly Pro Ile Gly Phe Arg Gly Pro Pro Gly
                245                 250                 255
Ile Pro Gly Ala Pro Gly Lys Ala Gly Asp Arg Gly Glu Arg Gly Pro
            260                 265                 270
Glu Gly Phe Arg Gly Pro Lys Gly Asp Leu Gly Arg Pro Gly Pro Lys
            275                 280                 285
Gly Thr Pro Gly Val Ala Gly Pro Ser Gly Glu Pro Gly Met Pro Gly
    290                 295                 300
Lys Asp Gly Gln Asn Gly Val Pro Gly Leu Asp Gly Gln Lys Gly Glu
305                 310                 315                 320
Ala Gly Arg Asn Gly Ala Pro Gly Glu Lys Gly Pro Asn Gly Leu Pro
                325                 330                 335
Gly Leu Pro Gly Arg Ala Gly Ser Lys Gly Glu Lys Gly Glu Arg Gly
            340                 345                 350
Arg Ala Gly Glu Leu Gly Glu Ala Gly Pro Ser Gly Glu Pro Gly Val
            355                 360                 365
Pro Gly Asp Ala Gly Met Pro Gly Glu Arg Gly Glu Ala Gly His Arg
    370                 375                 380
Gly Ser Ala Gly Ala Leu Gly Pro Gln Gly Pro Pro Gly Ala Pro Gly
385                 390                 395                 400
```

```
Val Arg Gly Phe Gln Gly Gln Lys Gly Ser Met Gly Asp Pro Gly Leu
            405                 410                 415
Pro Gly Pro Gln Gly Leu Arg Gly Asp Val Gly Asp Arg Gly Pro Gly
        420                 425                 430
Gly Ala Ala Gly Pro Lys Gly Asp Gln Gly Ile Ala Gly Ser Asp Gly
        435                 440                 445
Leu Pro Gly Asp Lys Gly Glu Leu Gly Pro Ser Gly Leu Val Gly Pro
        450                 455                 460
Lys Gly Glu Ser Gly Ser Arg Gly Glu Leu Gly Pro Lys Gly Thr Gln
465                 470                 475                 480
Gly Pro Asn Gly Thr Ser Gly Val Gln Gly Val Pro Gly Pro Pro Gly
            485                 490                 495
Pro Leu Gly Leu Gln Gly Val Pro Gly Val Pro Gly Ile Thr Gly Lys
        500                 505                 510
Pro Gly Val Pro Gly Lys Glu Ala Ser Glu Gln Arg Ile Arg Glu Leu
        515                 520                 525
Cys Gly Gly Met Ile Ser Glu Gln Ile Ala Gln Leu Ala Ala His Leu
        530                 535                 540
Arg Lys Pro Leu Ala Pro Gly Ser Ile Gly Arg Pro Gly Pro Ala Gly
545                 550                 555                 560
Pro Pro Gly Pro Pro Gly Pro Pro Gly Ser Ile Gly His Pro Gly Ala
            565                 570                 575
Arg Gly Pro Pro Gly Tyr Arg Gly Pro Thr Gly Glu Leu Gly Asp Pro
        580                 585                 590
Gly Pro Arg Gly Asn Gln Gly Asp Arg Gly Asp Lys Gly Ala Ala Gly
        595                 600                 605
Ala Gly Leu Asp Gly Pro Glu Gly Asp Gln Gly Pro Gln Gly Pro Gln
        610                 615                 620
Gly Val Pro Gly Thr Ser Lys Asp Gly Gln Asp Gly Ala Pro Gly Glu
625                 630                 635                 640
Pro Gly Pro Pro Gly Asp Pro Gly Leu Pro Gly Ala Ile Gly Ala Gln
            645                 650                 655
Gly Thr Pro Gly Ile Cys Asp Thr Ser Ala Cys Gln Gly Ala Val Leu
        660                 665                 670
Gly Gly Val Gly Glu Lys Ser Gly Ser Arg Ser Ser
        675                 680

<210> SEQ ID NO 4
<211> LENGTH: 107
<212> TYPE: DNA
<213> ORGANISM: Artificial Sequence
<220> FEATURE:
<223> OTHER INFORMATION: synthetic oligonucleotide

<400> SEQUENCE: 4
gtagagcacc gacagatcag cacattaagc aggtttgcat gagagtcata caagaacatt      60
ttgctgagat ggctgccagt cttaagcgtc cagactcagg tgccact                  107

<210> SEQ ID NO 5
<211> LENGTH: 111
<212> TYPE: DNA
<213> ORGANISM: Artificial Sequence
<220> FEATURE:
<223> OTHER INFORMATION: synthetic oligonucleotide

<400> SEQUENCE: 5
gggaaggagg ccagcgagca gcgcatccgt gagctgtgtg ggggatgat cagcgaacaa       60
```
attgcacagt tagccgcgca cctacgcaag cctttggcac ccgggtccat t        111

<210> SEQ ID NO 6
<211> LENGTH: 35
<212> TYPE: DNA
<213> ORGANISM: Artificial Sequence
<220> FEATURE:
<223> OTHER INFORMATION: synthetic oligonucleotide

<400> SEQUENCE: 6
tgcggatccg gtagagcacc gacagatcag cacat                          35

<210> SEQ ID NO 7
<211> LENGTH: 37
<212> TYPE: DNA
<213> ORGANISM: Artificial Sequence
<220> FEATURE:
<223> OTHER INFORMATION: synthetic oligonucleotide

<400> SEQUENCE: 7
gtcagtcgac ttaagtggca cctgagtctg gacgctt                        37

<210> SEQ ID NO 8
<211> LENGTH: 33
<212> TYPE: DNA
<213> ORGANISM: Artificial Sequence
<220> FEATURE:
<223> OTHER INFORMATION: synthetic oligonucleotide

<400> SEQUENCE: 8
tgcggatccg gccgggatgc cactgaccag cac                            33

<210> SEQ ID NO 9
<211> LENGTH: 37
<212> TYPE: DNA
<213> ORGANISM: Artificial Sequence
<220> FEATURE:
<223> OTHER INFORMATION: synthetic oligonucleotide

<400> SEQUENCE: 9
gtcagtcgac ttacaccgca cccagggctt cccgctt                        37

<210> SEQ ID NO 10
<211> LENGTH: 33
<212> TYPE: DNA
<213> ORGANISM: Artificial Sequence
<220> FEATURE:
<223> OTHER INFORMATION: synthetic oligonucleotide

<400> SEQUENCE: 10
tgcggatccg ggaaggaggc cagcgagcag cgc                            33

<210> SEQ ID NO 11
<211> LENGTH: 37
<212> TYPE: DNA
<213> ORGANISM: Artificial Sequence
<220> FEATURE:
<223> OTHER INFORMATION: synthetic oligonucleotide

<400> SEQUENCE: 11
gtcagtcgac ttaaatggac ccgggtgcca aaggctt                        37

<210> SEQ ID NO 12
<211> LENGTH: 40
<212> TYPE: DNA

<213> ORGANISM: Artificial Sequence
<220> FEATURE:
<223> OTHER INFORMATION: synthetic oligonucleotide

<400> SEQUENCE: 12
gtcaggatcc ggtgctagcg gtccgccagg accaccgggt                                40

<210> SEQ ID NO 13
<211> LENGTH: 49
<212> TYPE: DNA
<213> ORGANISM: Artificial Sequence
<220> FEATURE:
<223> OTHER INFORMATION: synthetic oligonucleotide

<400> SEQUENCE: 13
gtcagtcgac ttaaacacca ccacagcacg ggcctggtgg accaggagg                      49

<210> SEQ ID NO 14
<211> LENGTH: 60
<212> TYPE: DNA
<213> ORGANISM: Artificial Sequence
<220> FEATURE:
<223> OTHER INFORMATION: synthetic oligonucleotide

<400> SEQUENCE: 14 gggcccctg gtccgccagg accaccgggt ccacctggtc ctcctggtcc accaggcccg          60

<210> SEQ ID NO 15
<211> LENGTH: 44
<212> TYPE: DNA
<213> ORGANISM: Artificial Sequence
<220> FEATURE:
<223> OTHER INFORMATION: synthetic oligonucleotide

<400> SEQUENCE: 15
tgcggatccg gctatccggg tagagcaccg acagatcagc acat                          44

<210> SEQ ID NO 16
<211> LENGTH: 37
<212> TYPE: DNA
<213> ORGANISM: Artificial Sequence
<220> FEATURE:
<223> OTHER INFORMATION: synthetic oligonucleotide

<400> SEQUENCE: 16
gtcagctagc accagtggca cctgagtctg gacgctt                                  37

<210> SEQ ID NO 17
<211> LENGTH: 37
<212> TYPE: DNA
<213> ORGANISM: Artificial Sequence
<220> FEATURE:
<223> OTHER INFORMATION: synthetic oligonucleotide

<400> SEQUENCE: 17
gtcagctagc acccaccgca cccagggctt cccgctt                                  37

<210> SEQ ID NO 18
<211> LENGTH: 37
<212> TYPE: DNA
<213> ORGANISM: Artificial Sequence
<220> FEATURE:
<223> OTHER INFORMATION: synthetic oligonucleotide

<400> SEQUENCE: 18
gtcagctagc accaatggac ccgggtgcca aaggctt                                  37

<210> SEQ ID NO 19
<211> LENGTH: 38
<212> TYPE: PRT
<213> ORGANISM: Homo sapiens

<400> SEQUENCE: 19

Gly Ser Gly Arg Ala Pro Thr Asp Gln His Ile Lys Gln Val Cys Met
1               5                   10                  15

Arg Val Ile Gln Glu His Phe Ala Glu Met Ala Ala Ser Leu Lys Arg
            20                  25                  30

Pro Asp Ser Gly Ala Thr
        35

<210> SEQ ID NO 20
<211> LENGTH: 38
<212> TYPE: PRT
<213> ORGANISM: Homo sapiens

<400> SEQUENCE: 20

Gly Ser Gly Arg Asp Ala Thr Asp Gln His Ile Val Asp Val Ala Leu
1               5                   10                  15

Lys Met Leu Gln Glu Gln Leu Ala Glu Val Ala Val Ser Ala Lys Arg
            20                  25                  30

Glu Ala Leu Gly Ala Val
        35

<210> SEQ ID NO 21
<211> LENGTH: 39
<212> TYPE: PRT
<213> ORGANISM: Homo sapiens

<400> SEQUENCE: 21

Gly Ser Gly Lys Glu Ala Ser Glu Gln Arg Ile Arg Glu Leu Cys Gly
1               5                   10                  15

Gly Met Ile Ser Glu Gln Ile Ala Gln Leu Ala Ala His Leu Arg Lys
            20                  25                  30

Pro Leu Ala Pro Gly Ser Ile
        35

<210> SEQ ID NO 22
<211> LENGTH: 66
<212> TYPE: PRT
<213> ORGANISM: Artificial Sequence
<220> FEATURE:
<223> OTHER INFORMATION: synthetic peptide sequence

<400> SEQUENCE: 22

Gly Ser Gly Tyr Pro Gly Arg Ala Pro Thr Asp Gln His Ile Lys Gln
1               5                   10                  15

Val Cys Met Arg Val Ile Gln Glu His Phe Ala Glu Met Ala Ala Ser
            20                  25                  30

Leu Lys Arg Pro Asp Ser Gly Ala Thr Gly Ala Ser Gly Pro Pro Gly
        35                  40                  45

Pro Pro Gly Pro Pro Gly Pro Pro Gly Pro Pro Gly Pro Cys Cys Gly
    50                  55                  60

Gly Val
65

<210> SEQ ID NO 23

```
<211> LENGTH: 63
<212> TYPE: PRT
<213> ORGANISM: Artificial Sequence
<220> FEATURE:
<223> OTHER INFORMATION: synthetic peptide sequence

<400> SEQUENCE: 23

Gly Ser Gly Arg Asp Ala Thr Asp Gln His Ile Val Asp Val Ala Leu
1               5                   10                  15

Lys Met Leu Gln Glu Gln Leu Ala Glu Val Ala Val Ser Ala Lys Arg
            20                  25                  30

Glu Ala Leu Gly Ala Val Gly Ala Ser Gly Pro Pro Gly Pro Pro Gly
        35                  40                  45

Pro Pro Gly Pro Pro Gly Pro Pro Gly Pro Cys Cys Gly Gly Val
    50                  55                  60

<210> SEQ ID NO 24
<211> LENGTH: 64
<212> TYPE: PRT
<213> ORGANISM: Artificial Sequence
<220> FEATURE:
<223> OTHER INFORMATION: synthetic peptide sequence

<400> SEQUENCE: 24

Gly Ser Gly Lys Glu Ala Ser Glu Gln Arg Ile Arg Glu Leu Cys Gly
1               5                   10                  15

Gly Met Ile Ser Glu Gln Ile Ala Gln Leu Ala Ala His Leu Arg Lys
            20                  25                  30

Pro Leu Ala Pro Gly Ser Ile Gly Ala Ser Gly Pro Pro Gly Pro Pro
        35                  40                  45

Gly Pro Pro Gly Pro Pro Gly Pro Pro Gly Pro Cys Cys Gly Gly Val
    50                  55                  60
```

COMPOSITIONS COMPRISING THE NC2 DOMAIN OF COLLAGEN IX AND METHODS OF USING SAME

CROSS REFERENCE TO RELATED APPLICATIONS

The Present application is a continuation of PCT application PCT/US11/037,923, filed May 25, 2011, and claims the benefit of U.S. Ser. No. 61/348,735, filed May 26, 2010 both of which are hereby incorporated by reference in their entirety.

SEQUENCE LISTING

The specification further incorporates by reference the Sequence Listing submitted via EFS on Feb. 24, 2013. Pursuant to 37 C.F.R. §1.52(e)(5), the Sequence Listing text file, identified as 006910_5617SeqList.txt, is 26,415 bytes and was created on Feb. 22, 2013. The Sequence Listing, electronically filed herewith, does not extend beyond the scope of the specification and thus does not contain new matter.

FIELD OF THE INVENTION

The present invention relates to the newly identified timerization initiating and stagger determining capacity of the NC2 domain of collagen IX. The invention further relates to a hexavalent molecular building block wherein the linkage of heterologous moieties to the amino and carboxyl terminals of compositions comprising the NC2 domain of collagen IX promotes the directed association of those moieties via the trimerization initiating and stagger determining capacity of the NC2 domain.

BACKGROUND OF THE INVENTION

Collagen, the most abundant protein in the animal kingdom, is a naturally occurring fibrous protein that is found in the extracellular matrix and in connective tissue. Currently there are 28 known isoforms of collagen. Each collagen molecule is made up of three polypeptide strands called α-chains, which are themselves made up of collagenous (COL) and non-collagenous (NC) domains. One subset of the known collagen isoforms is the fibril associated collagens with interrupted triple helices (FACITs). This subset includes collagens type IX, XII, XIV, XVI, XIX, XX, XXI, and XXII. All FACIT collagens (except type XX) have at least two collagenous domains (COL1, COL2), and two non-collagenous domains (NC1, NC2), and the NC2 domain is positioned between the COL2 and COL1 domains. Although FACITs are generally composed of three identical α-chains, Collagen IX is a heterotrimer composed of three distinct α-chains: α1, α2, and α3.

Due to its unique properties, several attempts have been made to better understand the structure and function of the various domains of collagen IX, particularly in the context of the protein's timerization potential as well as the mode of its stagger selection. For example, reassociation of the chains of a pepsin-resistant low molecular weight (LMW) fragment of bovine collagen IX has been tested in vitro (14). The LMW fragment includes the sequence of COL1 and the beginning of NC1 with intact disulfides. Upon reduction and re-association followed by the formation of disulfide-bonded multimers only a negligible amount of α1α2α3 was observed (14). Another in vitro study was focused on either NC1 sequences or NC1 sequences extended with short fragments of COL1 (15). Whereas experiments with just NC1 sequences did not produce any significant amount of multimers, the extended sequences were partially successful and yielded ~10% of disulfide-bonded heterotrimeric α1α2α3 (15). On the other hand, a recent study of full-length and several deletion mutants expressed in insect cells showed that COL1 and NC1 are not required for trimerization of collagen IX, although COL1-NC1 region might be important for chain specificity (16). Additionally, the authors reported that the COL2-NC2 region of collagen IX is not sufficient for trimerization (16).

Given the lack of clarity regarding the timerization potential and stagger selection properties of the various domains of collagen IX, there exists a need in the art to identify the domain(s) mediating such properties. Once ascertained, the protein domain(s) mediating such properties can be employed in heterologous collagens to drive specific trimerization and stagger specificities, as well as in the production of molecular building blocks for the production of hexavalent targeting and/or therapeutic compositions. As described in detail below, the domain mediating the timerization potential and stagger selection properties of collagen IX is identified herein and the instant invention relates to compositions comprising that domain as well as uses thereof.

DETAILED DESCRIPTION OF THE INVENTION

It is shown for the first time that the NC2 domain of the heterotrimeric collagen IX promotes α-chain trimerization and stagger selection in a highly specific and effective manner. Previous attempts to attribute this role to either COL1 (14) or NC1. (15) showed only small amounts of the heterotrimer formed. Interestingly, single tripeptide unit deletions within the COL1 domain of the α3(IX) chain are known to not co-segregate with any disease phenotype and do not affect the formation of correctly folded heterotrimeric collagen IX, whereas similar deletions in type I collagen are lethal (23). With the primary role of NC2 in the folding initiation of collagen IX this discrepancy is now eliminated. Accordingly, the present invention relates to compositions and methods that take advantage of the newly identified timerization initiating and stagger determining capacity of the NC2 domain of collagen IX. For example, the present invention relates, in part, to a hexavalent molecular building block wherein the linkage of heterologous moieties to the amino and/or carboxyl terminals of monomers comprising the NC2 domain of collagen IX promotes the directed association of those moieties via the trimerization initiating and stagger determining capacity of the NC2 domain.

1. Collagen IX NC2 Domain Compositions
1.1. Collagen IX NC2 Domain Polypeptides

Figure 1:
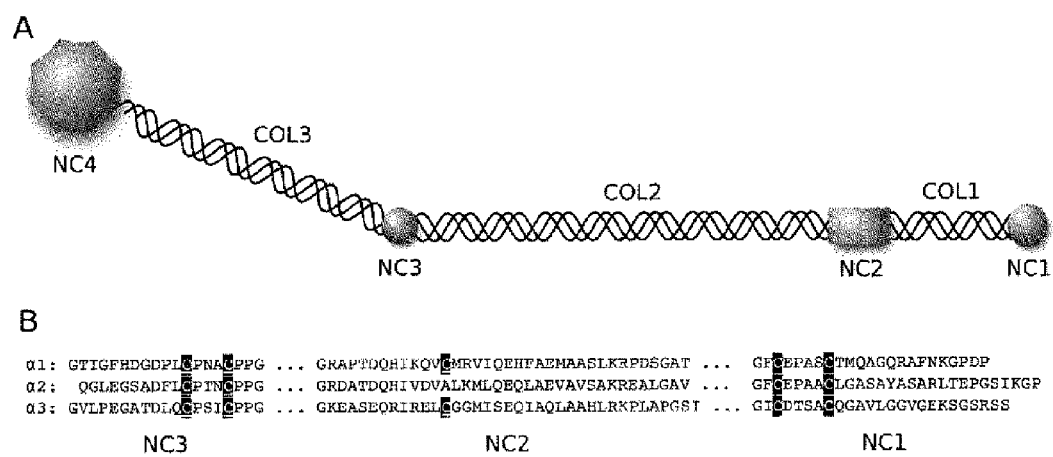
FIG. 1. Domains of collagen IX. A, Schematic presentation of collagen IX with three collagenous (COL1-COL3) and four non-collagenous (NC1-NC4) domains, numbered from the carboxyl-terminus. B, the amino acid sequences of NC3, NC2, and NC1 of human collagen IX of all three chains (Swiss-Prot numbers P20849 (SEQ ID NO. 1), Q14055 (SEQ ID NO. 2), Q14050 (SEQ ID NO. 3)). Cysteines in NC3 or NC1 form two cystine knots, each covalently cross-linking three chains (22).

In certain embodiments, the present invention relates to compositions comprising the amino acid sequences of the NC2 domain of collagen IX α1, α2, and α3 chains (see FIG. 1, SEQ ID NOs. 1, 2, and 3, respectively). In addition to polypeptide compositions comprising an amino acid sequence that is identical to SEQ. ID NOs. 1, 2, or 3, certain embodiments of the instant invention encompass polypeptide compositions comprising amino acid sequences that are "substantially similar" to SEQ. ID NO. 1, 2, or 3. Such polypeptide compositions include those sequences that retain certain structural and functional features of the NC2 domain of collagen IX α1, α2, and α3 chains, yet differ from the collagen IX α1, α2, and α3 chain amino acid sequences at one or more positions. Such polypeptide variants can be prepared by substituting, deleting, or adding amino acid residues from the original SEQ. ID NO. 1, 2 or 3 sequences via methods known in the art.

In certain embodiments, such substantially similar sequences include sequences that incorporate conservative amino acid substitutions. As used herein, a "conservative amino acid substitution" is intended to include a substitution in which the amino acid residue is replaced with an amino acid residue having a similar side chain. Families of amino acid residues having similar side chains have been defined in the art, including: basic side chains (e.g., lysine, arginine, histidine); acidic side chains (e.g., aspartic acid, glutamic acid); uncharged polar side chains (e.g., glycine, asparagine, glutamine, serine, threonine, tyrosine, cysteine); nonpolar side chains (e.g., alanine, valine, leucine, isoleucine, proline, phenylalanine, methionine, tryptophan); ft-branched side chains (e.g., threonine, valine, isoleucine); and aromatic side chains (e.g., tyrosine, phenylalanine, tryptophan, histidine). Other generally preferred substitutions involve replacement of an amino acid residue with another residue having a small side chain, such as alanine or glycine. Amino acid substituted peptides can be prepared by standard techniques, such as automated chemical synthesis.

In certain embodiments, a polypeptide of the present invention is at least about 70%, 71%, 72%, 73%, 74%, 75%, 76%, 77%, 78%, 79%, 80%, 81%, 82%, 83%, 84%, 85%, 86%, 87%, 88%, 89% 90%, 91%, 92%, 93%, 94%, 95%, 96%, 97%, 98%, or 99% homologous to the amino acid sequence of the NC2 domain of collagen IX α1, α2, and α3 chains (SEQ ID NOs:1, 2, or 3), and is capable of specific trimerization and stagger determination of the resulting triple helix. As used herein, the percent homology between two amino acid sequences is equivalent to the percent identity between the sequences. The percent identity between two sequences is a function of the number of identical positions shared by the sequences (i.e., % homology=# of identical positions/total # of positions×100), taking into account the number of gaps, and the length of each gap that need to be introduced for optimal alignment of the two sequences. The effect of the amino acid substitutions on the ability of the synthesized peptide to trimerize with other collagen IX NC2 domains, or variants thereof, and to determine the stagger of the triple helices can be tested using the methods disclosed in Examples section, below.

1.2. Nucleic Acids Encoding Collagen IX NC2 Domain Polypeptide

Another aspect of this disclosure pertains to isolated nucleic acid molecules that encode the NC2 domain of collagen IX α1, α2, or α3 chains of this disclosure, portions thereof; as well as complements of these nucleic acid molecules.

In other embodiments, the nucleic acid molecule of the invention is sufficiently complementary to a nucleotide sequence encoding a NC2 domain of collagen IX α1, α2, or α3 chains of this disclosure such that it can hybridize under stringent conditions to a nucleotide sequence encoding a NC2 domain of collagen IX α1, α2, or α3 chain of this disclosure, thereby forming a stable duplex.

In another embodiment, an isolated nucleic acid molecule of the present invention includes a nucleotide sequence which is at least about: 70%, 71%, 72%, 73%, 74%, 75%, 76%, 77%, 78%, 79%, 80%, 81%, 82%, 83%, 84%, 85%, 86%, 87%, 88%, 89% 90%, 91%, 92%, 93%, 94%, 95%, 96%, 97%, 98%, or 99%, or more homologous to a nucleotide sequence encoding a NC2 domain of collagen IX α1, α2, or α3 chain of this disclosure, or a portion, preferably of the same length, of such nucleotide sequence.

The nucleic acids may be present in whole cells, in a cell lysate, or in substantially pure form. A nucleic acid is "isolated" or rendered "substantially pure" when purified away from other cellular components or other contaminants, e.g., other cellular nucleic acids or proteins, by standard techniques, including alkaline/SDS treatment, CsCl banding, column chromatography, agarose gel electrophoresis and others well known in the art. A nucleic acid of this disclosure can be, for example, DNA or RNA and may or may not contain intronic sequences. In a preferred embodiment, the nucleic acid is a cDNA molecule.

Recombinant expression vectors which include the nucleic acids of the invention, and host cells transfected with such vectors, are also provided. As used herein, the term "vector" refers to a nucleic acid molecule capable of transporting another nucleic acid to which it has been linked and can include a plasmid, cosmid or viral vector. The vector can be capable of autonomous replication or it can integrate into a host DNA. Viral vectors include, e.g., replication defective retroviruses, adenoviruses and adeno-associated viruses. The expression vector can be a yeast expression vector, a vector for expression in insect cells, e.g., a baculovirus expression vector, or a vector suitable for expression in mammalian cells.

The recombinant expression vectors of the invention can be designed for expression of the NC2 domain of collagen IX α1, α2, or α3 chains of the invention in prokaryotic or eukaryotic cells. For example, the NC2 domain sequences of the invention can be expressed in *E. coli*, insect cells (e.g., using baculovirus expression vectors), yeast cells or mammalian cells. Suitable host cells are discussed further in Goeddel (108). Alternatively, the recombinant expression vector can be transcribed and translated in vitro, for example using T7 promoter regulatory sequences and T7 polymerase.

The term "host cell" and "recombinant host cell" are used interchangeably herein. Such terms refer not only to the particular subject cell but to the progeny or potential progeny of such a cell. Because certain modifications can occur in succeeding generations due to either mutation or environmental influences, such progeny may not, in fact, be identical to the parent cell, but are still included within the scope of the term as used herein. A host cell can be any prokaryotic or eukaryotic cell.

Vector DNA can be introduced into host cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation.

A host cell of the invention can be used to produce (i.e., express) a NC2 domain sequence of the invention. Accordingly, the invention further provides methods for producing a NC2 domain sequence of the invention using the host cells of the invention. In one embodiment, the method includes culturing the host cell of the invention (into which a recombinant expression vector encoding a NC2 domain sequence of the invention has been introduced) in a suitable medium such that a NC2 domain sequence of the invention is produced. In another embodiment, the method further includes isolating a NC2 domain sequence of the invention from the medium or the host cell.

Host cells transformed with nucleotide sequences encoding a NC2 domain sequence can be cultured under conditions suitable for the expression and recovery of the sequence from cell culture. The protein produced by a transformed cell may be located in the cell membrane, secreted or contained intracellularly depending on the sequence and/or the vector used. As will be understood by those of skill in the art, expression vectors containing polynucleotides that encode a collagen IX NC2 domain can be designed to contain signal sequences that direct secretion of the NC2 domain through a prokaryotic or eukaryotic cell membrane. As discussed in detail in sections 1.3.-1.4., below, other constructs can be used to join sequences encoding a NC2 domain sequence to nucleotide sequences encoding a polypeptide domain that will facilitate purification of soluble proteins. Such domains include, but are not limited to: metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.).

1.3. Heterologous Moieties Attached to Collagen IX NC2 Domain Polypeptides

In certain embodiments the polypeptide compositions of the instant invention comprise one or more heterologous moieties operably linked to the amino and/or carboxy terminals of a particular collagen IX NC2 domain. As used herein, "operable linkage" refers to the functional association of two compositions, such as the heterologous moieties and the NC2 domain compositions of the present invention, including, but not limited to associations mediated by one or more covalent or non-covalent bonds. Heterologous moieties that find use within the context of the instant invention include, but are not limited to: peptide and polypeptide sequences, including, but not limited to, diagnostic and/or therapeutic peptides and polypeptides, such as antibodies and peptide hormones; nucleic acid sequences, including, but not limited to, diagnostic and/or therapeutic nucleic acids, such as probes, antisense molecules, and siRNA molecules; polysaccharides, including, but not limited to, polysaccharides associated with eliciting immune responses, such as those that define bacterial serogroups; small molecule diagnostics and/or therapeutics, including, but not limited to, small molecule receptor agonists and antagonists, small molecule agonists or antagonists of enzyme function; and labels, including, but not limited to, contrast agents, fluorophores, enzymatic labels, and radioactive labels. In certain embodiments, a single collagen IX NC2 domain can be operably linked to two distinct heterologous moieties. In additional embodiments a homo- or heterotrimer of collagen IX NC2 domain compositions will comprise one to six heterologous moieties, where one, two, three, four, five, or all six heterologous moieties are the same or different.

In certain embodiments, the heterologous moiety is selected from one or more effector agents, such as, but not limited to, a diagnostic agent, a therapeutic agent, a chemotherapeutic agent, a radioisotope, an imaging agent, an anti-angiogenic agent, a cytokine, a chemokine, a growth factor, a drug, a prodrug, an enzyme, a binding molecule, a ligand for a cell surface receptor, a chelator, an immunomodulator, an oligonucleotide, a hormone, a photodetectable label, a dye, a peptide, a toxin, a contrast agent, a paramagnetic label, an ultrasound label, a pro-apoptotic agent, a liposome, a nanoparticle or a combination thereof.

In certain embodiments, the compositions of the instant invention comprise one or more heterologous peptide or polypeptide moieties, such as bacterial toxins, plant toxins, ricin, abrin, ribonucleases (RNase), DNase I, Staphylococcal enterotoxin-A, pokeweed antiviral protein, gelonin, diphtherin toxin, *Pseudomonas exotoxin, Pseudomonas* endotoxin, Ranpirnase (Rap), Rap (N69Q), PE38, dgA, DT390, PLC, tPA, a cytokine, a growth factor, a soluble receptor component, surfactant protein D, IL-4, sIL-4R, sIL-13R, VEGF121, TPO, EPO, clot-dissolving agents, enzymes, fluorescent proteins, sTNFα-R, avimers, antibodies, scFvs, dsFvs, and nanobodies.

In certain embodiments, the heterologous moiety operably linked to the collagen IX NC2 domain is an anti-angiogenic agent. Exemplary, but not limiting, anti-angiogenic agents of use in the context of the instant invention include, but are not limited to, angiostatin, baculostatin, canstatin, maspin, anti-VEGF antibodies or peptides, anti-placental growth factor antibodies or peptides, anti-Flk-1 antibodies, anti-Flt-1 antibodies or peptides, laminin peptides, fibronectin peptides, plasminogen activator inhibitors, tissue metalloproteinase inhibitors, interferons, interleukin 12, IP-IO, Gro-β, thrombospondin, 2-methoxyoestradiol, proliferin-related protein, carboxiamidotriazole, CMIOI, Marimastat, pentosan polysulphate, angiopoietin 2, interferon-alpha, herbimycin A, PNU145156E, 16K prolactin fragment, Linomide, thalidomide, pentoxifylline, genistein, TNP-470, endostatin, paclitaxel, accutin, angiostatin, cidofovir, vincristine, bleomycin, AGM-1470, platelet factor 4, and minocycline.

In still other embodiments, the heterologous moiety is selected from one or more therapeutic agents, such as, but not limited to, aplidin, azaribine, anastrozole, azacytidine, bleomycin, bortezomib, bryostatin-1, busulfan, calicheamycin, eamptothecin, 10-hydroxycamptothecin, carmustine, celebrex, chlorambucil, cisplatin, irinotecan (CPT-II), SN-38, carboplatin, cladribine, cyclophosphamide, cytarabine, dacarbazine, docetaxel, dactinomycin, daunomycin glucuronide, daunorubicin, dexamethasone, diethylstilbestrol, doxorubicin, 2-pyrrolinodoxorubieme (2P-DOX), cyano-morpholino doxorubicin, doxorubicin glucuronide, epirubicin glucuronide, ethinyl estradiol, estramustine, etoposide, etoposide glucuronide, etoposide phosphate, floxuridine (FUdR), 3',5'-O-dioleoyl-FudR (FUdR-dO), fludarabine, flutamide, fluorouracil, fluoxymesterone, gemcitabine, hydroxyprogesterone caproate, hydroxyurea, idarubicin, ifosfamide, L-asparaginase, leucovorin, lomustine, mechlorethamine, medroprogesterone acetate, megestrol acetate, melphalan, mercaptopurine, 6-mercaptopurine, methotrexate, mitoxantrone, mithramycin, mitomycin, mitotane, phenyl butyrate, prednisone, procarbazine, paclitaxel, pentostatin, PSI-341, semustine streptozocin, tamoxifen, taxanes, taxol, testosterone propionate, thalidomide, thioguanine, thiotepa, teniposide, topotecan, uracil mustard, velcade, vinblastine, vinorelbine, vincristine, ricin, abrin, ribonuclease, onconase, rapLR1, DNase 1, Staphylococcal enterotoxin-A, pokeweed antiviral protein, gelonin, diphtheria toxin, *Pseudomonas* exotoxin, and *Pseudomonas* endotoxin.

In certain embodiments, the heterologous moiety is can be selected from molecules capable of binding an antigen selected from the group consisting of CD2, CD3, CD8, CD10, CD21, CD23, CD24, CD25, CD30, CD33, CD37, CD38, CD40, CD48, CD52, CD55, CD59, CD70, CD74, CD80, CD86, CD138, CD147, HLA-DR, CEA, CSAp, CA-125, TAG-72, EFGR, HER2, HER3, HERO, IGF-IR, c-Met, PDGFR, MUC1, MUC2, MUC3, MUC4, TNFR1, TNFR2, NGFR, Fas (CD95), DR3, DR4, DR5, DR6, VEGF, PIGF, ED-B fibronectin, tenascin, PSMA, PSA, carbonic anhydrase IX, and IL-6.

In certain embodiments the heterologous moiety is a chemotherapeutic compound such as, but not limited to, 5-fluorouracil, bleomycin, busulfan, camptothecins, carboplatin, chlorambucil, cisplatin (CDDP), cyclophosphamide, dactinomycin, daunorubicin, doxorubicin, estrogen receptor binding agents, etoposide (VP 16), farnesyl-protein transferase inhibitors, gemcitabine, ifosfamide, mechlorethamine, melphalan, methotrexate, mitomycin, navelbine, nitrosurea, plicomycin, procarbazine, raloxifene, tamoxifen, taxol, temazolomide (an aqueous form of DTIC), transplatinum, vinblastine and methotrexate, vincristine, or any analog or derivative variant of the foregoing. Chemotherapeutic agents of use in the context of the instant invention that have activity against infectious organisms include, but are not limited to, acyclovir, albendazole, amantadine, amikacin, amoxicillin, amphotericin B, ampicillin, aztreonam, azithromycin, bacitracin, bactrim, Batrafen(R), bifonazole, carbenicillin, caspofungin, cefaclor, cefazolin, cephalosporins, cefepime, ceftriaxone, cefotaxime, chloramphenicol, cidofovir, Cipro(R), clarithromycin, clavulanic acid, clotrimazole, cloxacillin, doxycycline, econazole, erythrocycline, erythromycin, flagyl, fluconazole, flucytosine, foscaraet, furazolidone, ganciclovir, gentamycin, imipenem, isoniazid, itraconazole, kanamycin, ketoconazole, lincomycin, linezolid, meropenem, miconazole, minocycline, naftifine, nalidixic acid, neomycin, netilmicin, nitrofurantoin, nystatin, oseltamivir, oxacillin, paromomycin, penicillin, pentamidine, piperacillin-tazobactam, rifabutin, rifampin, rimantadine, streptomycin, sulfamethoxazole, sulfasalazine, tetracycline, tioconazole, tobramycin, tolciclate, tolnaftate, trimethoprim sulfamethoxazole, valacyclovir, vancomycin, zanamir, and zithromycin.

In certain embodiments the heterologous moiety is a label such as, but not limited to, an enzyme, a radioactive isotope, a fluorophor. In particular embodiments the label is an enzyme which involve the production of hydrogen peroxide and the use of the hydrogen peroxide to oxidize a dye precursor to a dye. Particular combinations include saccharide oxidases, e.g., glucose and galactose oxidase, or heterocyclic oxidases, such as uricase and xanthine oxidase, coupled with an enzyme which employs the hydrogen peroxide to oxidize a dye precursor, that is, a peroxidase such as horse radish peroxidase, lactoperoxidase, or microperoxidase. Among the preferred enzymes are the following: horseradish peroxidase, glucoamylase, alkaline phosphatase, glucose oxidase, and beta-D-galactosidase. In alternative embodiments, other enzymes may find use as the heterologous moiety, such as, but not limited to, hydrolases, transferases, and oxidoreductases, preferably hydrolyses such as alkaline phosphatase and beta-galactosidase. Alternatively luciferases may be used such as firefly luciferase and bacterial luciferase.

While the heterologous moieties of the invention have been described with reference to specific embodiments, it will be appreciated that various alternative moieties can be employed without departing from the invention.

1.4. Operable Linkage of Heterologous Moieties to Collagen IX NC2 Domain Polypeptides In certain embodiments the heterologous moiety is operably linked to the collagen IX NC2 domain via recombinant DNA technology. For example, in embodiments where the heterologous moiety is a peptide or polypeptide sequence, a nucleic acid sequence encoding that heterologous moiety can be introduced either upstream (for linkage to the amino terminus of the collagen IX NC2 domain) or downstream (for linkage to the carboxy terminus of the collagen IX NC2 domain), or both, of a nucleic acid sequence encoding the collagen IX NC2 domain of interest. Such fusion sequences comprising both the collagen IX NC2 domain encoding nucleic acid sequence and the heterologous moiety encoding nucleic acid sequence can be expressed using techniques well known in the art. Specific examples of such operable linkage to create fusion proteins comprising heterologous peptide and polypeptide moieties fused to collagen IX NC2 domains are included herein in Examples 1.1-1.3.

In certain embodiments the heterologous moiety is operably linked to the collagen IX NC2 domain via a chemical linker. Examples of such linkages typically incorporate 1-30 nonhydrogen atoms selected from the group consisting of C, N, O, S and P. Exemplary linkers include, but are not limited to, a substituted alkyl or a substituted cycloalkyl. Alternately, the heterologous moiety may be directly attached (where the linker is a single bond) to the amino or carboxy terminus of the NC2 domain. When the linker is not a single covalent bond, the linker may be any combination of stable chemical bonds, optionally including, single, double, triple or aromatic carbon-carbon bonds, as well as carbon-nitrogen bonds, nitrogen-nitrogen bonds, carbon-oxygen bonds, sulfur-sulfur bonds, carbon-sulfur bonds, phosphorus-oxygen bonds, phosphorus-nitrogen bonds, and nitrogen-platinum bonds. In certain embodiments, the linker incorporates less than 20 nonhydrogen atoms and are composed of any combination of ether, thioether, urea, thiourea, amine, ester, carboxamide, sulfonamide, hydrazide bonds and aromatic or heteroaromatic bonds. In certain embodiments, the linker is a combination of single carbon-carbon bonds and carboxamide, sulfonamide or thioether bonds.

In certain embodiments one or more heterologous moiety is attached at the amino and/or carboxy terminus of the NC2 domain. In alternative embodiments one or more heterologous moiety is attached at another amino acid position in the NC2 domain. Such alternative linkage of the heterologous moiety is limited only by the potential for the heterologous moiety to inhibit the NC2 domain's trimerization and stagger defining properties. In certain embodiments, the selection of an appropriate linker can reduce the potential of a heterologous moiety to interfere with the NC2 domain's trimerization and stagger defining properties. Furthermore, while the operable linkage of the heterologous moieties of the invention has been described with reference to specific embodiments, it will be appreciated that various alternative linkages can be employed without departing from the invention.

1.5. Pharmaceutical Compositions Comprising Collagen IX NC2 Domain Compositions

In another aspect, the present disclosure provides pharmaceutical compositions containing one or a combination of collagen IX NC2 domain compositions formulated together with a pharmaceutically acceptable carrier. Such compositions may include one or a combination of (e.g., two or more different) NC2 domain compositions comprising a NC2 domain sequence operably linked to a heterologous moiety of this disclosure. For example, in certain embodiments, a pharmaceutical composition of this disclosure can comprise a homo- or heterotimer of NC2 domain compositions comprising one to six heterologous moieties.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the active compound, i.e., the NC2 domain composition, can be coated in a material to protect the compound from the action of acids and other natural conditions that can inactivate the compound.

The pharmaceutical compounds of this disclosure may include one or more pharmaceutically acceptable salts. A "pharmaceutically acceptable salt" refers to a salt that retains the desired biological activity of the parent compound and does not impart any undesired toxicological effects (see e.g., Berge, S. M., et al. (1977) *J. Pharm. Sci.* 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A pharmaceutical composition of this disclosure also can include a pharmaceutically acceptable anti-oxidant. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Examples of suitable aqueous and nonaqueous carriers that may be employed in the pharmaceutical compositions of this disclosure include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of this disclosure is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Actual dosage levels of the active ingredients in the pharmaceutical compositions of the present disclosure may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present disclosure employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A composition of the present disclosure can be administered via one or more routes of administration using one or more of a variety of methods known in the art. As will be appreciated by the skilled artisan, the route and/or mode of administration will vary depending upon the desired results. Preferred routes of administration for collagen IX NC2 domain compositions of this disclosure include intravenous, intramuscular, intradermal, intraperitoneal, subcutaneous, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Alternatively, a collagen IX NC2 domain composition of this disclosure can be administered via a non-parenteral route, such as a topical, epidermal or mucosal route of administration, for example, intranasally, orally, vaginally, rectally, sublingually or topically.

The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

2. Methods of Using Collagen IX NC2 Domain Compositions 2.1. Methods of Directing Collagen Homo- and Hetertrimerization The availability of an effective collagen-specific heterotrimerization domain with three distinct chains opens the prospect of easy production of short native collagen fragments with chain composition control. For example, the collagen IX NC2 domain compositions of the instant invention can be used to introduced into the coding sequences of alternative collagen isotypes in order to control the composition of homo- and hetertrimers derived from such isotypes. This control can allow for the modulation of the resulting collagen trimer's interactions with its binding partners.

In one such example, collagen's interaction with cartilage oligomeric matrix protein (COMP) can be controlled via the use of the collagen IX NC2 domain compositions of the instant invention. COMP is a pentameric glycoprotein found in the extracellular matrix of cartilage (30), tendon (31) and ligament, where it is thought to play an important role in tissue development and homeostasis through interactions with cells (32) and collagens I and II (33). Mutations in COMP or collagen IX are known to result in phenotypes within the multiple epiphyseal dysplasia disease spectrum and suggested their interaction. Indeed, COMP was shown to interact with collagen IX and the binding sites were mapped to regions within or close to all four NC domains of collagen IX (34,35). Statistical analysis of COMP binding sites along collagen IX molecules using electron microscopy showed the highest frequency of occupation of the NC2 domain in the long isoform of collagen IX from cartilage and an even higher frequency for the short isoform (lacking the NC4 domain) from vitreous (34). Accordingly, the chain selection and heterotrimerization properties of the NC2 domain compositions of the instant invention can be used as a tool for a recombinant production of the correctly folded NC3 and NC1 domains, the other binding candidates for COMP.

In an alternative example, the collagen IX NC2 domain compositions of the instant invention can be employed to modulate collagen's interaction with glycosaminoglycans. Glycosaminoglycans play important roles in cell adhesion and extracellular matrix assembly. A remarkable binding of heparin to collagen IX was reported (36) and further analyzed (37,38). Full-length recombinant collagen IX has an apparent Kd of 3.6 nM for the heparin binding and electron microscopy suggests the presence of four heparin-binding sites located within or near all four NC domains (37). The heparin-binding ability of the NC4 domain was found to be rather moderate with a Kd of 0.6 µM (37) which emphasized the importance of other heparin-binding sites along the molecule. Whereas the NC4 domain is a product of the single α1 chain, all other domains are heterotrimeric and their production will again require the usage of the NC2 domain.

Similarly, the binding affinity of the matrilin-3 A-domain for type IX collagen was shown to be a few nM and the binding site was mapped to the amino-terminal part of COL3 (39). Detailed structural insight into this interaction can now be gained by an adequate design of heterotrimeric collagenous peptides spanning COL3 using the NC2 domain compositions of the instant invention.

2.2. Methods of Detection and/or Treatment Using Collagen IX NC2 Domain Compositions In certain embodiments the compositions of the present invention can find use in the detection, diagnosis and/or treatment of a disease or other medical condition. Such conditions may include, but are not limited to: infectious diseases, cancer, autoimmune diseases, and other genetic diseases. In certain embodiments detection, diagnosis, and/or treatment is mediated via the presence of one or more heterologous moieties capable of binding to a marker of such disease or medical condition, such as, but not limited to, a polypeptide, a nucleic acid, or a polysaccharide indicative of such disease or medical condition. In certain embodiments detection, diagnosis, and/or treatment is aided by the presence of one or more heterologous moieties capable of emitting, directly or indirectly, a detectable signal, such as, but not limited to, a fluorescent or enzymatic label. In certain embodiments treatment is aided by the presence of one or more heterologous moieties comprising a therapeutic agent, such as, but not limited to a chemotherapeutic, an antibiotic, or a radioisotope.

In certain embodiments, the compositions of the instant invention can be of use in the detection, diagnosis, and/or treatment of infection with pathogenic organisms, such as bacteria, viruses or fungi. Exemplary fungi that may be treated include *Microsporum, Trichophyton, Epidermopkyton, Sporothrix schenckii, Cryptococcus neoformans, Coccidioides immitis, Histoplasma capsulatum, Blastomyces dermatitidis* or *Candida albican*. Exemplary viruses include human immunodeficiency virus (HIV), herpes virus, cytomegalovirus, rabies virus, influenza virus, human papilloma virus, hepatitis B virus, hepatitis C virus, Sendai virus, feline leukemia virus, Reo virus, polio virus, human serum parvo-like virus, simian virus 40, respiratory syncytial virus, mouse mammary tumor virus, Varicella-Zoster virus, Dengue virus, rubella virus, measles virus, adenovirus, human T-cell leukemia viruses, Epstein-Barr virus, murine leukemia virus, mumps virus, vesicular stomatitis virus, Sindbis virus, lymphocytic choriomeningitis virus or blue tongue virus. Exemplary bacteria include *Bacillus anthracis, Streptococcus agalactiae, Legionella pneumophilia, Streptococcus pyogenes, Escherichia coli, Neisseria gonorrhoeae, Neisseria meningitidis, Pneumococcus* spp., *Hemophilis influenzae* B, *Treponema pallidum, Lyme disease spirochetes, Pseudomonas aeruginosa, Mycobacterium leprae, Brucella abortus, Mycobacterium tuberculosis* or a *Mycoplasma*.

In certain embodiments, the compositions of the instant invention can be used for the detection, diagnosis, and/or therapeutic treatment of cancer. It is anticipated that any type of tumor and any type of tumor antigen may be targeted by operably linking one or more appropriate heterologous moieties to the collagen IX NC2 domain polypeptide. Exemplary types of tumors that may be targeted include acute lymphoblastic leukemia, acute myelogenous leukemia, biliary cancer, breast cancer, cervical cancer, chronic lymphocytic leukemia, chronic myelogenous leukemia, colorectal cancer, endometrial cancer, esophageal, gastric, head and neck cancer, Hodgkin's lymphoma, lung cancer, medullary thyroid cancer, non-Hodgkin's lymphoma, multiple myeloma, renal cancer, ovarian cancer, pancreatic cancer, glioma, melanoma, liver cancer, prostate cancer, and urinary bladder cancer.

Tumor-associated antigens that may be targeted by one or more appropriate heterologous moiety operably linked to the collagen IX NC2 domain polypeptide include, but are not limited to, carbonic anhydrase IX, A3, antigen specific for A33 antibody, BrE3-antigen, CD1, CDIa, CD3, CD5, CD15, CD16, CD19, CD20, CD21, CD22, CD23, CD25, CD30, CD45, CD74, CD79a, CD80, HLA-DR, NCA 95, NCA90, HCG and its subunits, CEA (CEACAM-5), CEACAM-6, CSAp, EGFR, EGP-1, EGP-2, Ep-CAM, Ba 733, HER2/neu, hypoxia inducible factor (HIF), KC4-antigen, KS-1-antigen, KS1-4, Le-Y, macrophage inhibition factor (MIF), MAGE, MUC1, MUC2, MUC3, MUC4, PAM-4-antigen, PSA, PSMA, RS5, S100, TAG-72, p53, tenascin, IL-6, IL-8, insulin growth factor-1 (IGF-I), Tn antigen, Thomson-Friedenreich antigens, tumor necrosis antigens, VEGF, placenta growth factor (PlGF), 17-1A-antigen, an angiogenesis marker (e.g., ED-B fibronectin), an oncogene marker, an oncogene product, and other tumor-associated antigens. Additional reports on tumor associated antigens include Mizukami et al., (2005, Nature Med. 11:992-97); Hatfield et al., (2005, Curr. Cancer Drug Targets 5:229-48); Vallbohmer et al. (2005, J. Clin. Oncol. 23:3536-44); and Ren et al. (2005, Ann. Surg. 242:55-63), each of which is incorporated herein by reference.

In certain embodiments, the compositions of the instant invention can be of use in the detection, diagnosis, and/or treatment of autoimmune diseases such as, but not limited to: amyotrophic lateral sclerosis (ALS, Lou Gehrig's Disease), ankylosing spondylitis, asthma, Crohn's disease, Cushing's syndrome, eczema, fibromyalgia, irritable bowel syndrome, lupus, lyme disease, multiple sclerosis, psoriasis, rheumatoid arthritis, and scleroderma.

In certain embodiments, the compositions of the instant invention can be of use in the detection, diagnosis, and/or treatment of genetic diseases, such as, but not limited to: canavan disease, celiac disease, cystic fibrosis, Down syndrome, Duchenne muscular dystrophy, haemophilia, Klinefelter's syndrome, neurofibromatosis, phenylketonuria, sickle-cell disease, Tay-Sachs disease, and Turner syndrome.

While the use of the compositions of the instant invention has been described with reference to specific embodiments, it will be appreciated that various alternative methods and uses can be employed without departing from the invention.

EXAMPLES

The present invention will be better understood by reference to the following Examples, which are provided as exemplary of the invention, and not by way of limitation.

Example 1

1.1. Cloning of Trx_α1NC2, Trx_α2NC2 and Trx_α3NC2

To facilitate expression of short sequences comprising the NC2 domain of human collagen IX, the sequences were cloned as parts of fusion molecules with a His-tagged thioredoxin sequence containing a thrombin cleavage site (HisTag-Trx-thr) to cleave off products later. Initially, DNA encoding HisTag-Trx-thr was recloned from the vector pHisTrx2 (18) into pET23d(+) (Novagen) using NcoI and BamHI restriction sites. The resulting plasmid, pET23-HisTrx, had multiple cloning sites just after the HisTag-Trx-thr gene. All constructs in this study were cloned and expressed using the plasmid pET23-HisTrx.

The plasmid (clone ID 5248739, NCBI accession number BC041479), containing an incomplete sequence of the human collagen IX α2 chain was purchased from Open Biosystems (USA) and used as a template for PCR. Two other templates, encoding α1 or α3 NC2 domains, were synthetic oligonucleotides: 5'-GGTAGAGCACCGACAGATCAGCACATTAAGCAGGTTTGCATGAGAGTCATACAAGAAC-ATTTTGCTGAGATGGCTGCCAG TCTTAAGCGTCCA-GACTCAGGTGCCACT-3' (SEQ ID NO. 4) for α1 and 5'-GGGAAGG AGGCCAGCGAGCAGCGCATC CGTGAGCTGTGTGGGGGGATGATCAGCGAACAAATT GCACAGTTAGCCGCGCACCTA CGCAAGCCTTTGG-CACCCGGGTCCATT-3' (SEQ ID NO. 5) for α3. The latter contained two modified codons (underlined sequences) for arginine, they replaced codons that are rare in *E. coli*. Sequences encoding human collagen IX NC2 domain were PCR amplified using the following set of oligonucleotide pairs, forward and reversed, respectively: 5'-TGC GGATCCGGTAGAGCACCGACAGATCAGCACAT-3' (SEQ ID NO. 6) and 5'-GTCA GTCGACTTAAGTGGCACCTGAGTCTGGACGCTT-3' (SEQ ID NO. 7) for α1, 5'-TGC GGATCCGGCCGGGATGCCACTGACCAGCAC-3' (SEQ ID NO. 8) and 5'-GTCA GTCGACTTACACCGCACCCAGGGCTTCCCGCTT-3' (SEQ ID NO. 9) for α2, 5'-TGCGGATCCGGGAAGGAGGCCAGCGAGCAGCGC-3' (SEQ ID NO. 10) and 5'-GTCA GTCGACTTAAATGGACCCGGGTGCCAAAGGCTT-3' (SEQ ID NO. 11) for α3. Underlined sequences are BamHI and SalI restriction sites for forward and reversed primers, respectively. PCR products were cloned into the pET23-HisTrx vector using the restriction sites BamHI and SalI. The DNA inserts were verified by Sanger dideoxy DNA sequencing.

1.2. Cloning of Trx_α1NC2-(GPP)₅CC, Trx_α2NC2-(GPP)₅CC and Trx_α3NC2-(GPP)₅CC

Constructs with collagenous sequences were prepared as follows. A DNA fragment encoding the collagenous sequence and the collagen III cystine knot was PCR amplified using oligonucleotides: 5'-GTCA GGATCCGGTGC-TAGCGGTCCGCCAGGACC ACCGGGT-3' (SEQ ID NO. 12) (forward, BamHI site is underlined, NheI site is in bold) and 5'-GTCA GTCGACTTAAACACCACCACAGCA-CGGGCCTGGTGGACCAGGAGG-3' (SEQ ID NO. 13) (reversed, SalI site is underlined), and a synthetic oligonucleotide as a template: 5'-GGGCCCCCTGGTCCGCCAGGAC-CACCGGGTCCACCTGGTCCTCCTGGTCCACCAGGC CCG-3' (SEQ ID NO. 14). The PCR product was cloned into the pET23-HisTrx vector using restriction sites BamHI and SalI. The DNA insert was verified by Sanger dideoxy DNA sequencing. The resulting plasmid, pET23-HisTrx-GPP5CC, was used to clone three chains of NC2 using the restriction sites BamHI and NheI. For that, fragments of the NC2 chains were PCR amplified using the same forward primers for α2 and α3, the new forward primer for α1: TGC GGATCCGGCTATCCGGGTAGAGCACCGACAGAT-CAGCACAT (SEQ ID NO. 15) (BamHI site is underlined, extra sequence encoding tripeptide unit GYP is in bold) and the following reversed primers (NheI site is underlined): 5'-GTCA GCTAGCACCAGTGGCACCTG AGTCTG-GACGCTT-3' (SEQ ID NO. 16) for α1, 5'-GTCA GCTAGCACCCACCGCACCCAG GGCTTCCCGCTT-3' (SEQ ID NO. 17) for α2, 5'-GTCA GCTAGCACCAATGGACCCGGG TGCCAAAGGCTT-3' (SEQ ID NO. 18) for α3.

1.3. Expression of Proteins and Initial Purification

The recombinant proteins were expressed separately in the *E. coli* BL21(DE3) host strain (Novagen). Colonies from freshly transformed competent cells were resuspended in 2×TY media (16 g tryptone, 10 g yeast extract and 5 g NaCl per liter), grown to $OD_{600}$ ~0.6-0.8 and induced by adding IPTG to a final concentration of 1 mM. The constructs without collagenous sequence were expressed at 25° C. for 16-20 h. Cells containing the constructs with collagenous sequence were initially grown at 25° C., transferred to 4° C. and expressed for 7-10 days.

Each construct was initially purified separately. Cells were harvested by centrifugation, resuspended in 20 mM Tris/HCl buffer, pH 8, and disrupted by ultrasonication. After the sonication the buffer was adjusted to 100 mM Tris/HCl buffer, pH 8, containing 200 mM NaCl, 10 mM imidazole, by adding appropriate amounts of stock solutions. Debris was removed by centrifugation at 15,000 g for 30 minutes and the lysate was incubated with the Ni-NTA Resin (Qiagen) at room temperature for 30 minutes. The Ni-NTA Resin with bound protein was loaded into a column, allowed to drain and thoroughly washed with the wash buffer (50 mM Na-phosphate buffer, pH8, containing 500 mM NaCl, 20 mM imidazole). The protein was eluted with the elution buffer (50 mM Na-phosphate buffer, pH 8, containing 500 mM NaCl and 500 mM imidazol).

1.4. Oxidative Folding

Initially the purified constructs either with or without collagenous part were folded under the same oxidative conditions. The three chains of approximately equal concentrations were mixed, diluted with water and the buffer was adjusted to 100 mM Tris/HCl buffer, pH 8.6, containing 15 mM Na-phosphate, 150 mM NaCl, 150 mM imidazol, 10 mM reduced glutathione, 1 mM oxidized glutathione at 25° C. Final concentration of each chain was ~10 M. The solution was sequentially incubated at 37° C. for 24 hours, at 30° C. for 24 hours, 25° C. for 24 hours and the pH value was periodically checked and adjusted to be not lower than 8.3. Finally, the solution was extensively dialyzed against 50 mM Tris/HCl buffer, pH 8, containing 150 mM NaCl, at room temperature to remove imidazol and reducing agents.

1.5. Thrombin Cleavage and Removal of Thioredoxin

Thrombin cleavage was performed at 4° C. for 48 hours with recombinant thrombin protease (BaculoGold™, BD Biosciences) in 50 mM Tris/HCl buffer, pH 8.0, supplemented with 150 mM NaCl. The final concentration of thrombin was 1 U/ml or 17 μg/ml (based on the information of the manufacturer). The resulting fragments of interest had two additional amino acid residues GS before the native amino acid sequence (Table 1). Thrombin cleaved material was run over the Ni-NTA resin to separate NC2-containing fragments from His-tagged thrombin or uncleaved material. The NC2-containing fragments were eluted with 20 mM imidazol, 50 mM Na phosphate, 500 mM NaCl, pH 7.2.

1.6. Final Purification

Two additional purification steps were applied for the NC2-containing products, namely, cation- and anion-exchange columns. First, the starting material was extensively dialyzed against 50 mM HEPES buffer, pH 7, loaded onto the SP-sepharose column (GE Healthcare) and eluted with a linear gradient of NaCl (0 to 0.6M). The major peak was observed at 0.25-0.3M NaCl and its fractions were pooled for the next purification step. The fractions were combined and extensively dialyzed against 20 mM Tris/HCl, pH8, loaded onto the Q-sepharose column (GE Healthcare) and eluted with a linear gradient of NaCl (0 to 200 mM). The major peak was eluted at 40-50 mM NaCl and its fractions were pooled. To eliminate proteolytic contamination an extra purification step was applied to the α123NC2 complex. Fractions after the anionexchange column were combined and loaded onto the Phenyl-sepharose column (GE Healthcare) in 50 mM Na phosphate buffer (pH 7.2), supplemented with 1M of ammonium sulfate. The complex was eluted with 0.5M ammonium sulfate in 50 mM Na phosphate buffer (pH7.2), the rest of material was eluted with much lower concentrations of ammonium sulfate and the majority of proteolytic contamination was eluted only with 8M urea.

Amino acid compositions and protein concentrations were determined in triplicate after hydrolysis in 6M HCl (22 h at 110° C.) using a Beckman 6300 amino acid analyzer.

1.7. HPLC and MS Analysis

HPLC analysis was performed on a HP 1090 Liquid Chromatograph with a detection wavelengths of 215 nm. Chromatographic separation was achieved by gradient elution on a 5 µm pore size 2.1 mm×150 mm Zorbax 300SB-C18 column. LC-MS analysis was performed on a Waters Q-TOF Micro Mass Spectrometer with an ESI ionization source coupled to a Waters nanoAcquity HPLC system. Samples were loaded onto a 5 µm pore size 180 µm×20 mm Symmetry C18 trapping column. Chromatographic separation was achieved by gradient elution off the trapping column onto a 1.7 µm 100 µm×100 mm BEH130 C18 analytical column at a flow rate of 0.8 µL/min. Raw MS data was processed using Waters MassLynx software and deconvoluted using the maximum entropy algorithm MaxEnt 1.

1.8. Analytical Ultracentrifugation

Sedimentation equilibrium measurements were performed with a Beckman model XLA analytical ultracentrifuge. Absorbance was measured at 240 nm. Runs were carried out at 20° C. in an An60-Ti rotor using 12 mm cells and Epon, 2 channels, centerpieces. Speeds used were 22,000 or 25,000 r.p.m. for α123NC2-(GPP)$_5$CC or α123NC2, respectively. Data analysis was done using Ultrascan II (version 9.3). Partial specific volumes were calculated using individual sequences of peptides and averaged; the values were 0.725 or 0.732 cm$^3$ g-1 for α123NC2-(GPP)$_5$CC or α123NC2, respectively.

1.9. Circular Dichroism Analysis

CD spectra were recorded on an AVIV model 202 spectropolarimeter (AVIV Instruments, Inc.) with thermostatted quartz cells of 1-5 mm path length. The spectra were normalized for concentration and path length to obtain the mean molar residue ellipticity after subtraction of the buffer contribution. Thermal scanning curves were recorded at 222 nm for the α123NC2 complex to monitor the α-helical secondary structure transition or at 230 nm for α123NC2-(GPP)$_5$CC to monitor the collagen triple helix transition. Peptide concentrations were determined by amino acid analysis.

1.10. Evaluation of the Thermodynamic Data

CD transition curves of the α123NC2 complex were interpreted based on a two-state mechanism where two unfolded chains, U13 (α1-α3) and U2 (α2), associate into a native complex, n:

U13+U2 ↔ N

The equilibrium constant $K_N$ is:

$$K_N = [N]/([U13][U2]) \quad (1)$$

where [N] is concentration of the native complex; [U13] and [U2] are concentrations of unfolded α1-α3 and α2, respectively.

The two mass conservations are defined by $c_0 13=[U13]+[N]$ and $c_0 2=[U2]+[N]$. For the complex with $[U13]=[U2]$ the two total concentrations are equal $c_0=c_0 13=c_0 2$. Equation 1 can be rewritten as:

$$K_N=F/(c_0(1-F)2) \quad (2)$$

where F is the fraction of folded complex:

$$F=[N]/c_0$$

From equation 2:

$$F=w-(w^2-1)^{1/2} \quad (3)$$

where $w=1+1/(2K_N c_0)$.

The measured CD signal is connected with F by the relation:

$$[\Theta]=(a_N+b_N T)F+(a_U+b_U T)(1-F) \quad (4)$$

where parameters $a_N$, $b_N$ and $a_U$, $b_U$ account for the linear temperature dependencies of dichroism signals of the native and unfolded state, respectively.

The equilibrium constant is related with the standard Gibbs free energy $\Delta G^0$, the standard enthalpy $\Delta H^0$ and the standard entropy $\Delta S^0$ of the transition by:

$$K_N=\exp(-\Delta G^0/(RT))=\exp(-(\Delta H^0-T\Delta S^0)/(RT)) \quad (5)$$

Assuming that $\Delta H^0$ and $\Delta S^0$ are constant within the temperature interval of the transition, the global fit of equation 4 using relations from equations 3 and 5 allowed to determine the standard enthalpy, $\Delta H^0$, and the standard enthropy, $\Delta S^0$. The parameters $a_N$, $b_N$, $a_u$, $b_u$, $\Delta H^0$, and $\Delta S^0$ were fitted simultaneously.

From equations 2 and 5 the midpoint of the transition ($T_m$), where F=0.5, it follows:

$$T_m=\Delta H^0/(\Delta S^0 \pm R\ln(0.5c_0)) \quad (6)$$

1.11. Results 1.11.1. Results: Design of Constructs

Constructs containing the NC2 regions of three human collagen IX chains (α1, α2, or α3) either extended or not with a collagen triple helical sequence ending with the cystine knot of collagen III (Table 1) were cloned as part of a fusion molecule. The fusion molecule comprised a His-tagged thioredoxin followed by a thrombin cleavage sequence and a fragment of interest (18). The cystine knot of collagen III (19) was used as a folding marker for the triple helix formation. It was shown earlier that two cysteines in each chain form interchain disulfide bonds only after the triple helix is folded (20). By covalently linking three collagenous chains it allows an easy detection of a trimeric band on SDS-PAGE under nonreducing conditions. As a collagenous sequence we used a short stretch of only five GPP units (Table 1).

TABLE 1

Sequences, calculated molar masses and pI values of the individual peptides.
The sequences are shown for individual peptides after the cleavage of the thioredoxin part. Molar
masses, $M_W$, are calculated for reduced cysteines.

| Peptide | Sequence | M(Da) | pI |
|---|---|---|---|
| α1NC2 | GSGRAPTDQHIKQVCMRVIQEHFAEMAASLKRPDSGAT | 4124.6 | 8.21 |
| α2NC2 | GSGRDATDQHIVDVALKMLQEQLAEVAVSAKREALGAV | 3977.5 | 4.95 |
| α3NC2 | GSGKEASEQRIRELCGGMISEQIAQLAAHLRKPLAPGSI | 4103.7 | 8.21 |
| α1NC2-(GPP)$_5$CC | GSGYPGRAPTDQHIKQVCMRVIQEHFAEMAASLKRPDSGATGAS(GPP)$_5$GPCCGGV | 6487.3 | 7.96 |
| α2NC2-(GPP)$_5$CC | GSGRDATDQHIVDVALKMLQEQLAEVAVSAKREALGAVGAS(GPP)$_5$GPCCGGV | 6022.8 | 4.95 |
| α3NC2-(GPP)$_5$CC | GSGKEASEQRIRELCGGMISEQIAQLAAHLRKPLAPGSIGAS(GPP)$_5$GPCCGGV | 6149.0 | 7.96 |

1.11.2. Results: Bacterial Expression of Fusion Proteins

Temperature optimization was required to obtain similar expression levels of different constructs. The most problematic were constructs containing the α2 chain sequences. Finally, constructs without collagenous sequence were expressed at 25° C., whereas constructs with collagenous sequence required prolonged expression at 4° C. Although, all constructs were expressed separately, they produced only soluble proteins. The yields were sufficient and were estimated to be 20-50 mg of a fusion protein starting from 1 L of bacterial media.

Figure 2:
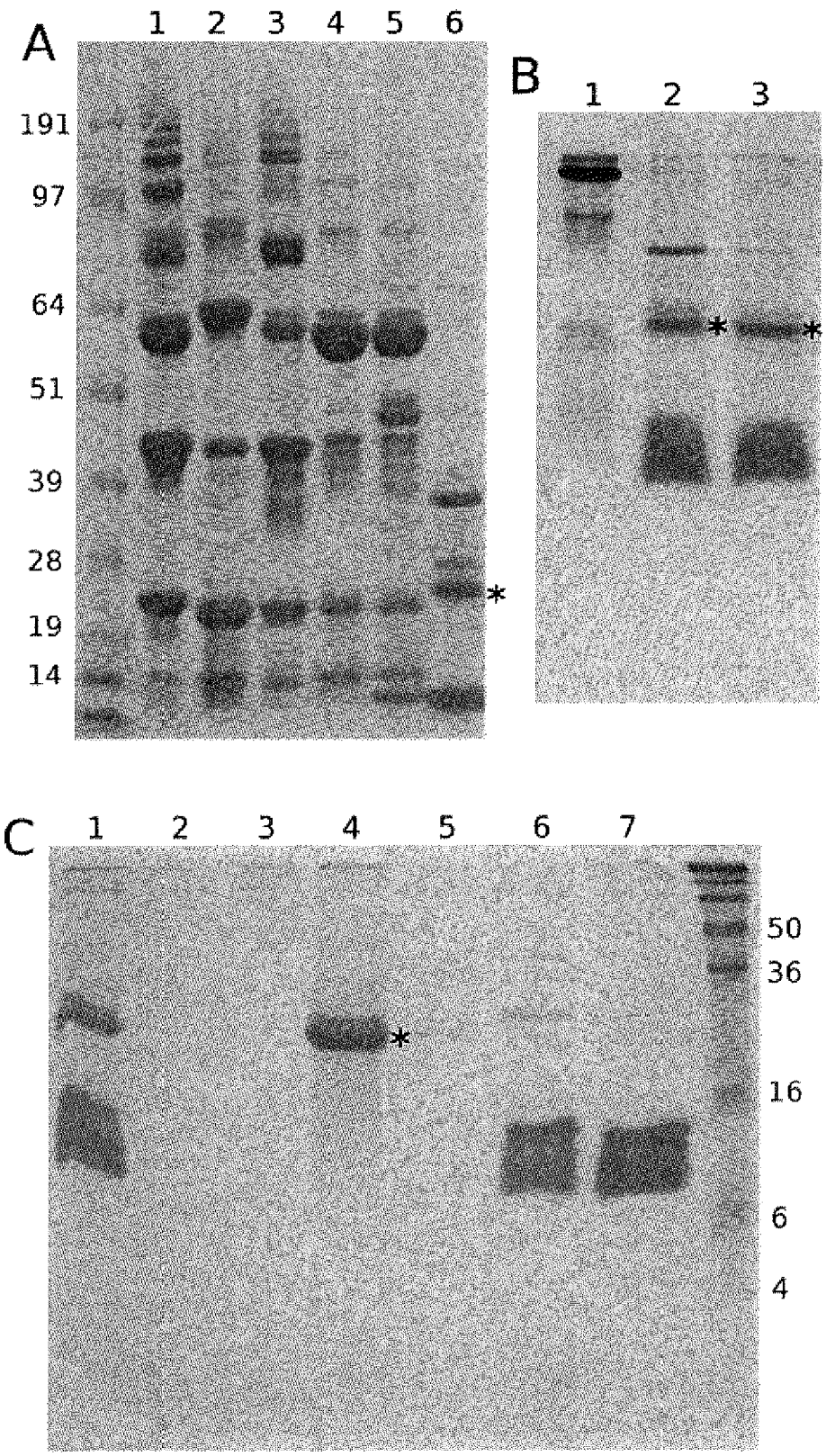
FIG. 2. Initial purification, reoxidation, cleavage and separation of α123NC2-(GPP)$_5$CC. A, non-reduced samples analyzed on 4-12% NuPAGE MOPS (Invitrogen). Lanes 1-3, separate elutes of α1NC2-(GPP)$_5$CC, α2NC2-(GPP)$_5$CC, and α3NC2-(GPP)$_5$CC from the Ni-NTA resin (Qiagen); lane 4, the reoxidized mix of α1NC2-(GPP)$_5$CC, α2NC2-(GPP)$_5$CC, and α3NC2-(GPP)$_5$CC; lanes 5 and 6, thrombin cleavage products of the reoxidized mix at 30 mins and 16 hrs. B, Thrombin cleavage products analyzed on 15% Tris-Glycine SDS-PAGE under non-reducing conditions. Lane 1, non-cleaved material; lanes 2 and 3, cleaved products at 16 and 36 hrs. C, The purification of the thrombin cleaved products over the Ni-NTA resin (Qiagen) and the analysis on 15% Tris-Glycine SDS-PAGE under non-reducing conditions. Lane 1, loading material; lanes 2 and 3, flow through and wash with loading buffer; lane 4, 20 mM imidazol elute, that presumably contains α123NC2-(GPP)$_5$CC; lanes 5-7, 40, 60, and 500 mM imidazol elutes. Bands with α123NC2-(GPP)$_5$CC are marked with a star.

1.11.3. Results: Initial Purification of Fusion Proteins Trx_α1NC2-(GPP)$_{5C}$C, Trx_α2NC2-(GPP)$_5$CC and Trx_α3NC2-(GPP)$_5$CC and their Reoxidation Soluble fractions of cell lysates were separately purified over the Ni-NTA resin and analyzed on a gel (FIG. 2A, lanes 1-3). In addition to bands corresponding to monomeric species around 20 kDa, dimeric, trimeric and ladders of higher multimers were observed, indicating formation of multiple intermolecular disulfide bonds, presumably due to misfolding. When equimolar amounts (~10 μM) of all three constructs were combined and reoxidized using reduced and oxidized glutathiones as reshuffling agents, one predominant trimeric band was observed on a gel under non-reducing conditions (FIG. 2A, lane 4).

1.11.4. Results: Thrombin Cleavage of Oxidized Trx_α123NC2-(GPP)$_5$CC and Thioredoxin Removal Thrombin cleavage of the oxidized material showed gradual removal of one, two and finally all three thioredoxin parts from the trimeric band (FIG. 2A, lanes 5 and 6; FIG. 2B, lanes 2 and 3). The resulting band corresponding to a trimer without thioredoxin moieties (with an apparent mass of ~20 kDa) is marked with a star in FIGS. 2A and 2B. Separation of the cleaved thioredoxin part bearing the his-tag from the NC2-containing trimer was performed using the Ni-NTA resin (FIG. 2C). The moderate binding of the NC2-containing trimer to the Ni-NTA resin was presumably due to several histidine residues in the NC2 sequences (Table 1).

1.11.5. Results: Purification and MS Analysis of α123NC2-(GPP)$_5$CC

Figure 3:
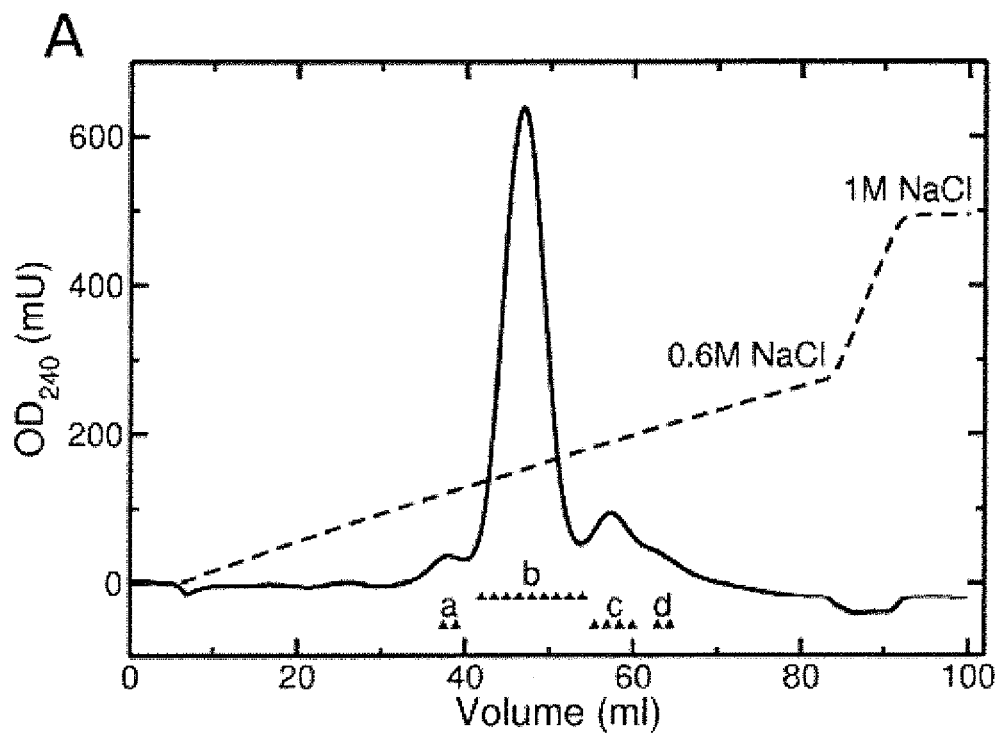
FIG. 3. Purification of α123NC2-(GPP)$_5$CC using SP-sepharose. A, chromatogram. Fractions labeled with a, b, c, and d were analyzed on a gel. B, Analysis of the fractions on 4-12% NuPAGE MOPS (Invitrogen) under non-reducing conditions. Lane 1, loading; lane 2, flow through; lane 3, fraction a; lanes 4-11, fractions b; lanes 12-14, fractions c; lane 15, fraction d.
Figure 3:
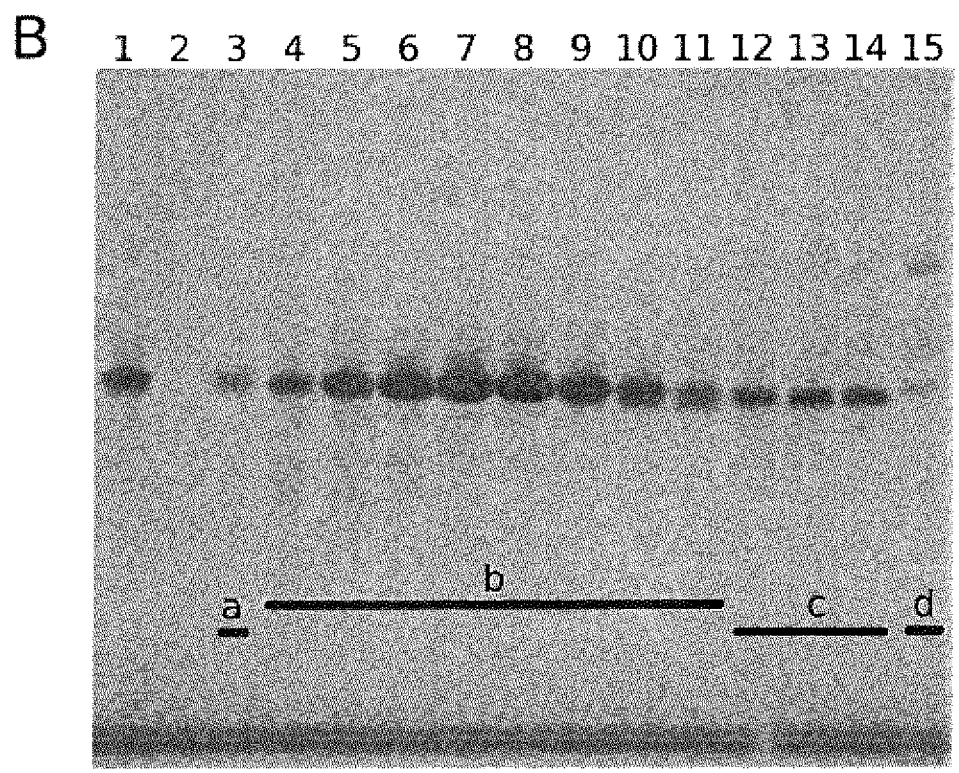
Figure 4:
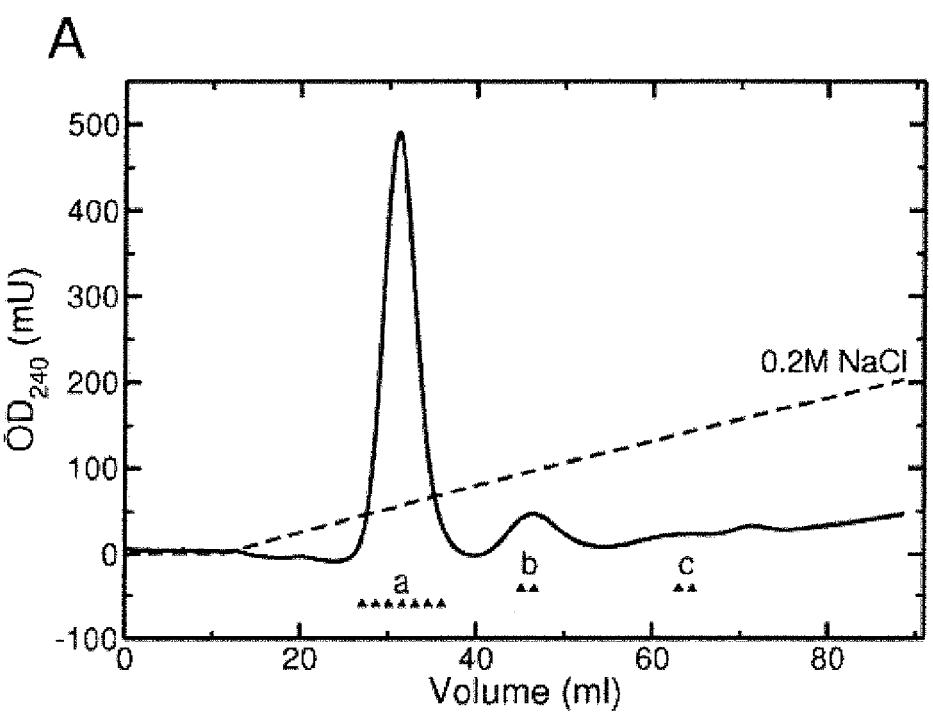
FIG. 4. Purification of α123NC2-(GPP)$_5$CC using SP-sepharose. A, chromatogram. Fractions labeled with a, b and c were analyzed on a gel. B, Analysis of the fractions on 4-12% NuPAGE MOPS (Invitrogen) under non-reducing conditions. Lane 1, loading; lane 2, flow through; lanes 3-8, fractions a; lane 9, fraction b; lanes 10, fraction c.
Figure 4:
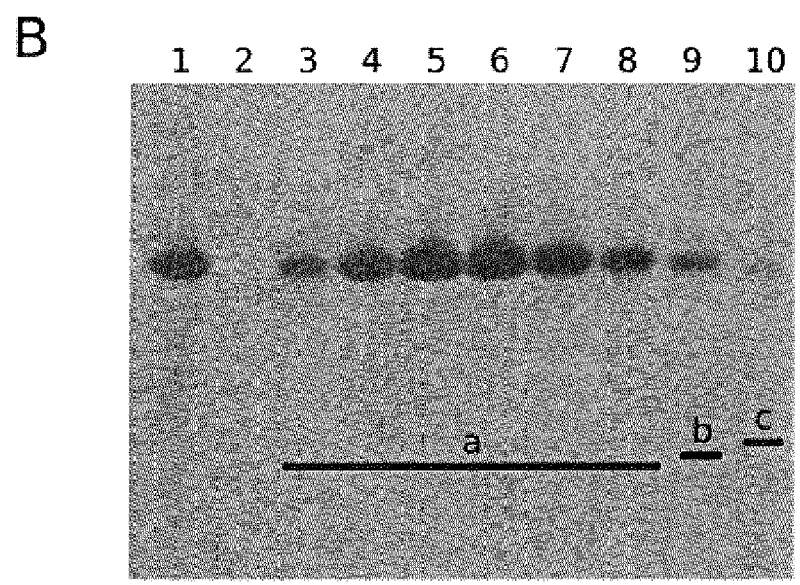
Figure 5:
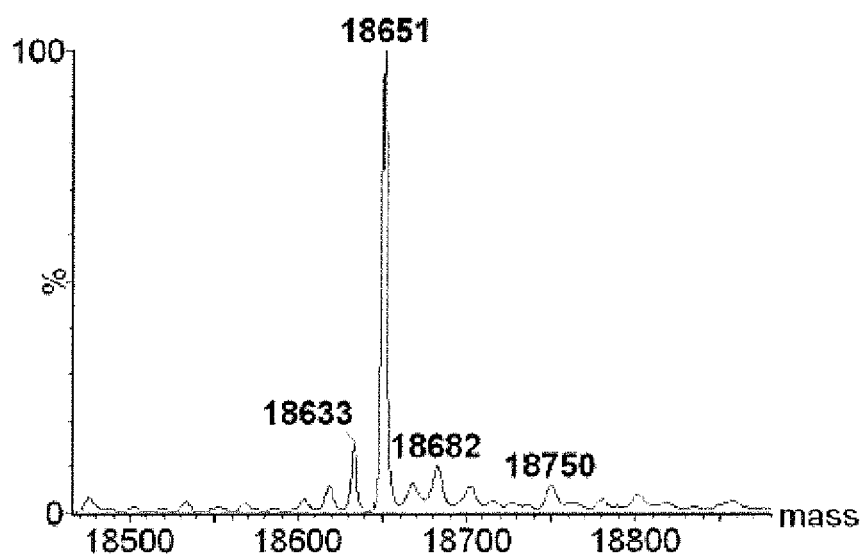
FIG. 5. Deconvoluted mass spectra of α123NC2-(GPP)$_5$CC. The 18651 peak corresponds to α123NC2-(GPP)$_5$CC.

It was concluded that different calculated pI values of the NC2 sequences (Table 1) might be effectively used to separate possible different combinations of α chains. A single major peak was observed in consequent runs over the cation- and anion-exchange columns (FIGS. 3 and 4). Finally, the MS analysis of the purified trimer showed a molar mass of 18650.5Da, which is only consistent with the oxidized heterotrimeric complex, α123NC2-(GPP)$_5$CC (FIG. 5, Table 2).

TABLE 2

Mass spectrometry and sedimentation equilibrium data.
Molar masses, $M_W$, were calculated for oxidized cystines.
Sedimentation equilibrium runs were performed at 20° C.
in 50 mM Na phosphate, 150 mM NaCl, pH 8. Concentrations
of complexes were 0.25 mg/ml or 0.12 mg/ml for α123NC2-
(GPP)$_5$CC or α123NC2, respectively.

| Complex | Calculated $M_W$(Da) | Mass Spectrometry (Da) | Sedimentation equilibrium (kDa) |
|---|---|---|---|
| α123NC2-(GPP)$_5$CC | 18651.1 | 18650.5 | 18.1 ± 3.6 |
| α123NC2 | 8226.3 + 3977.5 = 12203.8 | 8226.0; 3977.0 | 10.8 ± 2.0 |

1.11.6. Results: Production and Analysis of α123NC2

Figure 6:
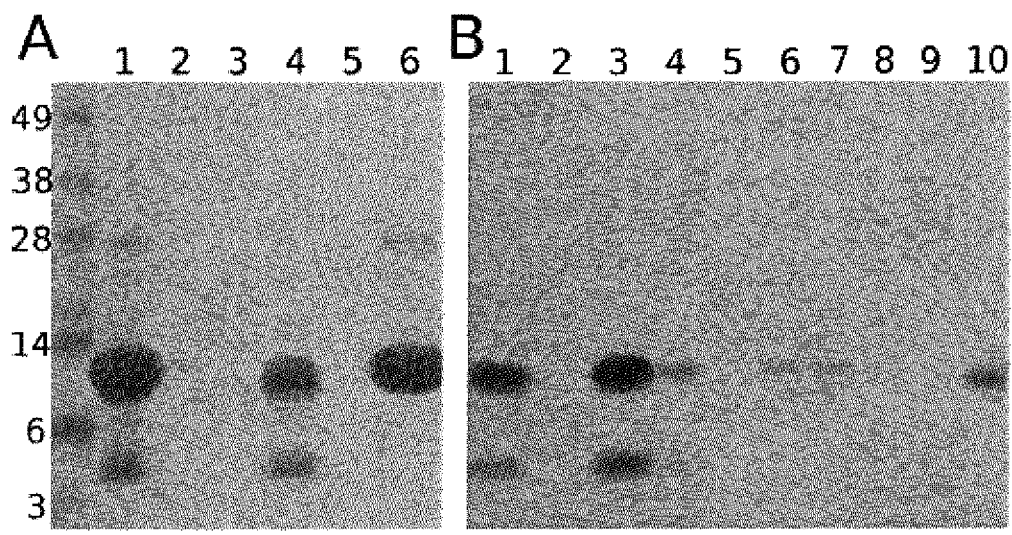
FIG. 6. Purification of α123NC2. A, Separation of thrombin cleavage products using the Ni-NTA resin (Qiagen) analyzed on 4-12% NuPAGE MES (Invitrogen) under non-reducing conditions. Lane 1, loading; lane 2 and 3, flow through and washing with loading buffer; lane 4, 20 mM imidazol elute, that contains α123NC2; lanes 5 and 6, 40 and 500 mM imidazol elutes. B, Final purification of α123NC2 using the Phenyl-sepharose column (GE Healthcare) analyzed on 4-12% NuPAGE MES (Invitrogen) under nonreducing conditions. Lane 1, loading with 1M ammonium sulfate; lane 2, flow through; lanes 3 and 4, elutes with 0.5 and 0.3M ammonium sulfate; lanes 5-8, elutes with 0.2, 0.1, 0.05, and 0M ammonium sulfate, respectively; lanes 9 and 10, elutes with 1 and 8M urea. Two bands of the α123NC2 complex observed under non-reducing conditions presumably correspond to a single chain of α2NC2 and a disulfide cross-linked product of chains α1NC2 α3NC2.
Figure 7:
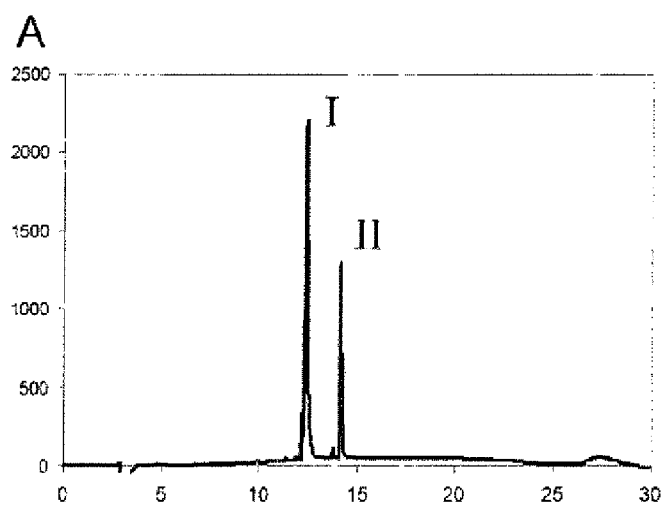
FIG. 7. Analytical HPLC and mass spectroscopy of α123NC2. HPLC analysis of α123NC2 produced two major peaks (A). LC-MS was performed on the sample and the mass spectrum obtained for peak 1 (B) corresponds to α1NC2-α3NC2 and that of peak II (C) to α2NC2. The inset in (B) shows the absence of masses corresponding to α1NC2-α1NC2 and α3NC2-α3NC2.
Figure 7:
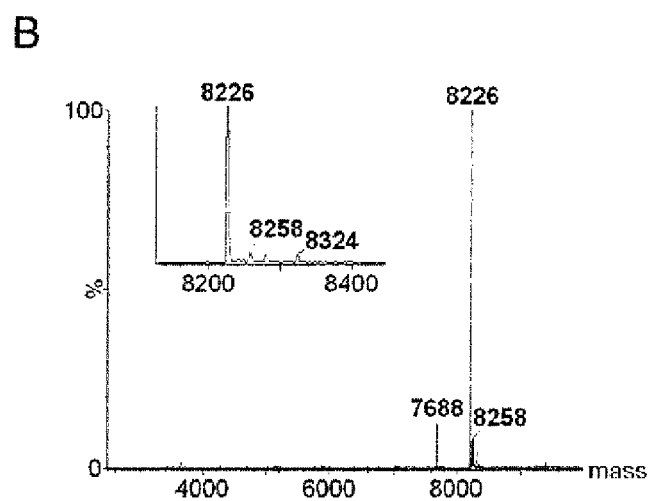
Figure 7:
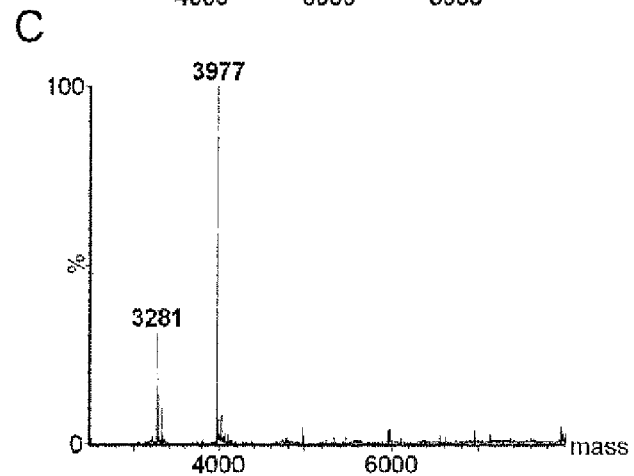

The same strategy was applied for constructs without collagenous sequence and the collagen III cystine knot. Since these constructs lacked the ability to form covalently linked trimers, only monomeric and dimeric bands were observed on a denaturing gel under non-reducing conditions (data not shown). After the thrombin cleavage the NC2-containing complex also showed binding to the Ni-NTA resin and was eluted using the same imidazol concentration (FIG. 6A). Again, two bands were observed under non-reducing conditions, one at ~4 kDa and another at ~9 kDa (FIG. 6A, lane 4). The complex was further purified using the cation and anion-exchange columns, analogously to α123NC2-(GPP)$_5$CC. Additional purification step using the Phenyl-sepharose column was necessary to remove impurities and/or proteolytic fragments (FIG. 6B). Most of contamination was only eluted with 8M urea (FIG. 6B, lane 10). The complex was run over the analytical C18 HPLC and two major peaks were observed following the absorbance of peptide bonds at 215 nm (FIG. 7A). The ratio of areas for those peaks was 2:1. The MS analysis of the peaks identified molar masses of 8226.0 and 3977.0 Da, respectively (FIGS. 7B and C), which corresponds to disulfide-bonded α1NC2-α3NC2 and dissociated α2NC2 (Table 2). These data supports the formation of the heterotrimeric α123NC2 complex with disulfide-linked α1 and α3 chains and the right stoichiometry of chains.

1.11.7. Results: Sedimentation Equilibrium Analysis

The oligomeric state of the purified heterotrimeric complexes, α123NC2-(GPP)$_5$CC or α123NC2, were analyzed by analytical ultracentrifugation. Sedimentation equilibrium runs at 20° C. in phosphate-buffer saline, pH 8, revealed trimeric organization for both complexes (Table 2). Although, the determined trimeric masses were within the error limits of the experiment, the values were less then expected in both cases. This discrepancy could probably be due to an underestimation of the partial specific volumes used for the analysis. The calculation of partial specific volumes were based on the amino acid composition, whereas disulfide bonds are known to notably increase the value of the partial specific volume.

1.11.8. Results: Secondary Structure Content and Thermal Transitions

Figure 8:
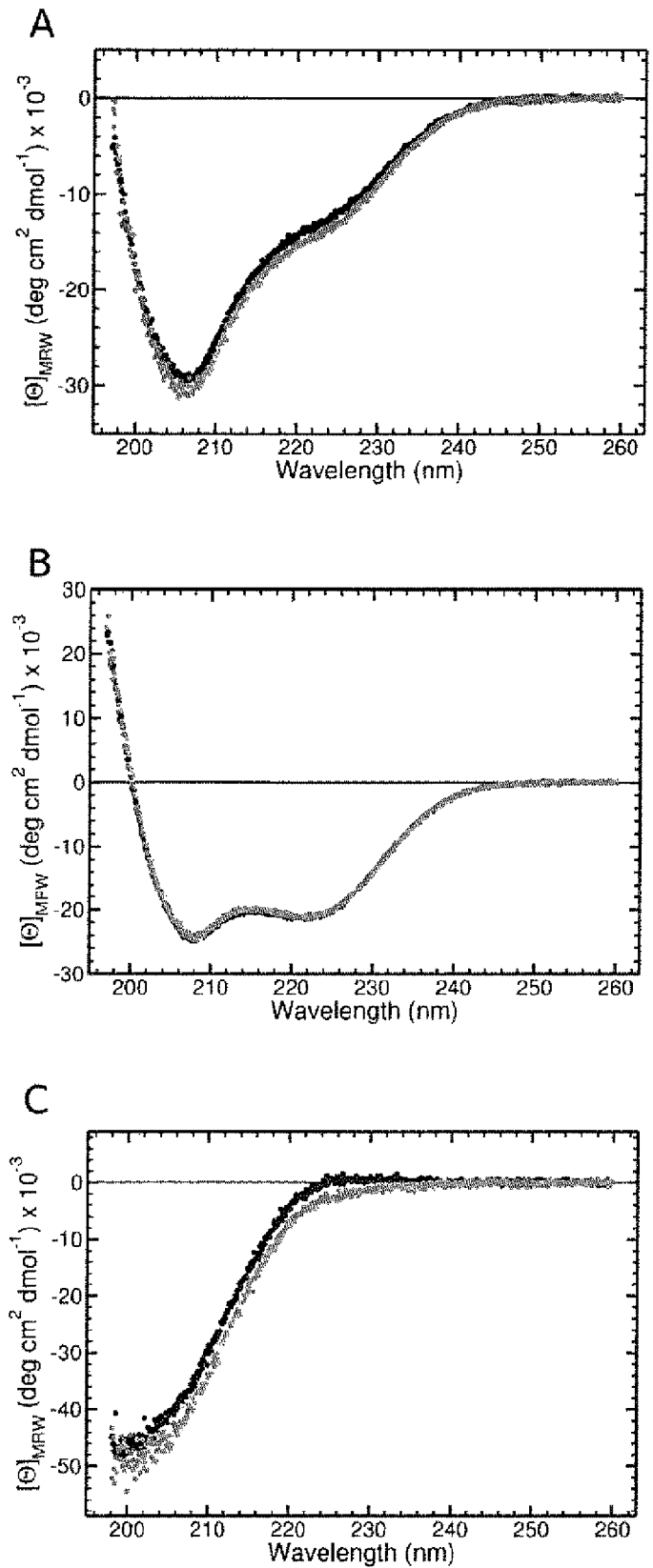
FIG. 8. Circular dichroism spectroscopy of the NC2-containing complexes. A, CD spectra of α123NC2-(GPP)$_5$CC recorded in 50 mM sodium phosphate buffer, pH 8, (black circles) and in 50 mM sodium acetate buffer, pH 4.5, (patterned circles) using 7 μM complex concentrations and a 1-mm path length quartz cuvette equilibrated at 20° C. B, CD spectra of α123NC2 recorded in 50 mM sodium phosphate buffer, pH 8, (black circles) and in 50 mM sodium acetate buffer, pH 4.5, (patterned circles) using 18.7 μM complex concentrations and a 1-mm path length quartz cuvette equilibrated at 20° C. C, calculated spectra of the collagenous part of α123NC2-(GPP)$_5$CC in two buffers, respectively.

The far ultraviolet CD spectra of α123NC2-(GPP)$_5$CC or α123NC2 in buffers with two different pH values are shown in FIG. 8. Notably, they are similar to the spectra reported previously for (GPP)$_{10}$-containing NC2 or just NC2 of homotrimeric collagen XIX (6). The α123NC2 complex has predominantly an α-helical structure (FIG. 8B), whereas α123NC2-(GPP)$_5$CC demonstrates superimposition of α-helical and collagen triple-helical structures (FIG. 8A). Equimolar subtraction of the α123NC2 spectrum from the α123NC2-(GPP)$_5$CC spectrum and subsequent adjustment of the mean molar ellipticity demonstrates the presence of the collagen triple helical structure (FIG. 8C).

Figure 9:
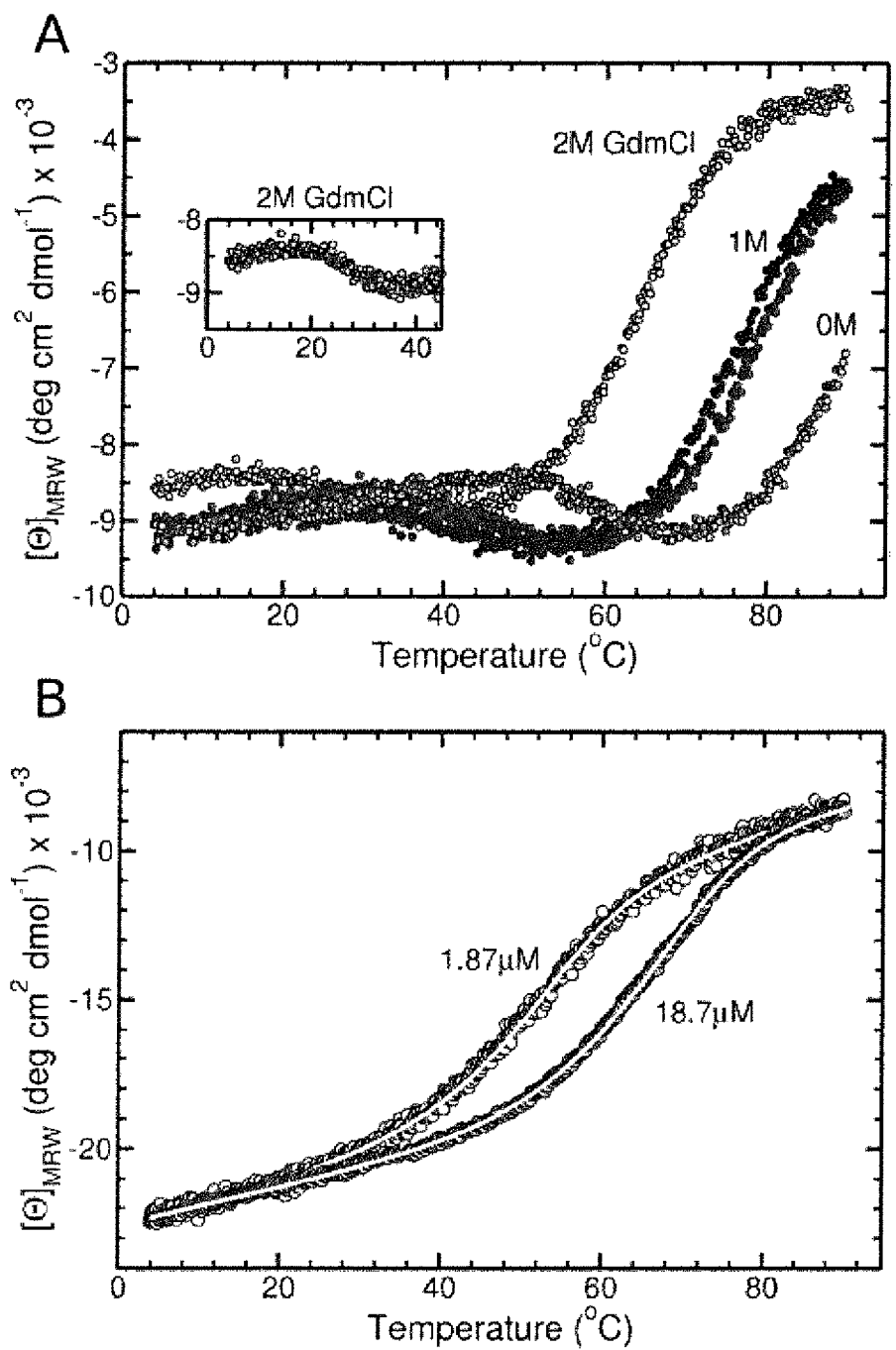
FIG. 9. Thermal transitions of the NC2-containing complexes. A, Thermal transition curves of α123NC2-(GPP)$_5$CC were recorded in 50 mM sodium acetate buffer, pH 4.5, supplemented with 0M (green circles), 1M (red circles for heating and blue circles for cooling), and 2M (cyan circles) guanidine hydrochloride using 7 μM complex concentrations and a 1-mm path length quartz cuvette. The change in collagen triple helical and α-helical contents was monitored at 230 nm with a scan rate of PC/min. Heating and cooling transition curves are shown for the sample with 1M guanidine hydrochloride to demonstrate the reversibility of the transition. The first transition followed by the increase of the CD signal is associated with the unfolding of the collagen triple helix, whereas the second transition is associated with the unfolding of the NC2 domain. B, Thermal transition curves of α123NC2 were recorded in 50 mM sodium acetate buffer, pH 4.5, using two complex concentrations, 1.87 (yellow circles) or 18.7 μM (brown circles), and 5- or 1-mm path length quartz cuvettes, respectively. The change in α-helical content was monitored at 222 nm with a scan rate of 0.25° C./min. The curves were globally fitted (white lines) as described herein.

The thermal stability of the complexes was studied at pH 4.5 to prevent disulfide bond reshuffling upon denaturation. Thermal denaturations were also observed at pH 8 with similar transitions upon heating, but refolding curves upon cooling deviated significantly. Transitions at pH 4.5 showed full reversibility and were further analyzed (FIG. 9). The α123NC2-(GPP)$_5$CC complex was monitored at 230 nm to maximize a change in the collagen triple helix content upon transitions. Nevertheless, a change in the α-helical content remained significant and allowed to simultaneously monitor both possible transitions (FIG. 9A). The second transition was not completed at 90° C. (FIG. 9A, in green) and required addition of guanidine hydrochloride to fully resolve both transitions in the available temperature range. The midpoint transition temperature values, $T_m$, of both transitions were shifted to lower temperature due to the denaturing effect of guanidine hydrochloride. The first transition followed by a decrease in the signal upon heating is associated with the melting of the collagen triple helix (6), whereas the second transition is linked to the unfolding of the α-helical NC2 domain. According to the change in the α-helical content (the second transition) in buffer supplemented with either 1 or 2M guanidine hydrochloride, only about a half of the transition of the NC2 domain was observed in the plain buffer, thus, the $T_m$ value of the NC2 domain in the α123NC2-(GPP)$_5$CC complex is ~90° C. The $T_m$ value of the collagen triple helix is ~59° C., which demonstrates impressive dual stabilizing effect of the NC2 domain on one side and the cystine knot on the opposite side. Compare it with $T_m$=58° C. for the NC2 domain of collagen XIX linked to (GPP)$_{10}$, NC2(GPP)$_{10}$ (6), where the stabilizing role of the NC2 domain is possibly the same, but the collagenous part is much longer and lacks the cystine knot.

In contrast to the α123NC2-(GPP)$_5$CC complex, where no dependence on concentration for the $T_m$ values was observed, the melting transitions of the α123NC2 complex showed a remarkable decrease in $T_m$ upon decreasing the concentration (FIG. 9B). This dependence demonstrated that the loss of α-helicity was coupled with the dissociation of α1NC2-α3NC2 and α2NC2. Since the α1NC2 chain is disulfide-linked to the α3NC2 chain, only two products dissociates from the complex upon denaturation and the folding reaction should be considered as bimolecular. According to this and other assumptions (see 1.1.-1.10., above), two transitions using a 10-fold difference in concentrations of the complex were separately globally fitted and yielded similar values of the standard enthalpy, $\Delta H°$, and the standard entropy, $\Delta S°$. Namely, for 18.7 μM: $T_m$=65.8° C., $\Delta H°$=−202.8 kJ/(mol complex), $\Delta S°$=−502 J/(mol complex K); for 1.87 μM: $T_m$=51.2° C., $\Delta H°$=−199.6 kJ/(mol complex), $\Delta S°$=−500 J/(mol complex K). To achieve the $T_m$ value of ~90° C. observed for the α123NC2-(GPP)$_5$CC complex the concentration of the α123NC2 complex was estimated to be ~2 mM based on Equation 6. This again emphasizes the stabilizing role of the cystine knot within the α123NC2-(GPP)$_5$CC complex despite the collagenous sequence separating it from the NC2 domain. Similar stabilizing effects are expected from the natural cystine knots located within the NC3 and NC1 domains.

Example 2

Hexavalent Molecular Building Block with Stagger Determining Specificity

As described in detail above, the NC2 domain compositions are hexavalent multimerization domains that allow for specific attachment of, for example, one to six heterologous moieties. Furthermore, the NC2 domain compositions are capable of trimerizing to form heterotrimeric molecules, wherein each trimer consists of an α1, α2, and an α3 chain. In forming such heterotrimers, the individual α-chains can take on one of six distinct registers (α1–α2–α3; α1–α3–α2; α2–α1–α3; α2–α3–α1; α3–α1–α2; or α3–α2–α1) wherein the amino acids of the individual chains are staggered by one amino acid residue. The stagger determining function of the NC2 domain can be identified by performing the following experiments.

2.2. NMR Analysis of the NC2 Domain of Type IX Collagen

Three different sequences of Gly-Xaa-Yaa (where Xaa and Yaa or distinct amino acids) are prepared for NMR analysis and repeating units of the particular sequences are attached to either the amino-terminal or carboxy-terminal of each of the NC2 domain sequences of type IX collagen. As outlined below, heterotrimers are then formed and the resulting trimers are analyzed by NMR to determine the stagger of the triple helices formed adjacent to the NC2 domain. This can be done either with synthetic peptides or by expression of constructs in suitable host cells, such as, but not limited to, E. coli. The peptide synthesis route allows for the incorporation of 4(R) hydroxyproline in the Yaa position, which has a stabilizing effect on the triple helix.

2.2.1. Peptide Synthesis and Sample Preparation

All peptides can be synthesized with an Advanced Chemtech Apex 396 solid phase peptide synthesizer using standard Fmoc (N-(9-fluorenyl)methoxycarbonyl) chemistry and a Rink 4-methylbenzhydrylamine-amide resin and can be N-terminally acetylated and C-terminally amidated. Uniformly labeled amino acids can be purchased form Cambridge Isotope Laboratories. Purification is performed on a Varian PrepStar220 high pressure liquid chromatograph using a preparative reverse phase $C_{18}$ column with a linear gradient of water and acetonitrile, each containing 0.5% trifluoroacetic acid and analyzed by matrix-assisted laser desorption ionization time-of-flight mass spectrometry on a Bruker Autoflex II.

NMR samples are prepared in a 9:1 ratio of $H_2O$ to $D_2O$, and a 10 mM phosphate buffer to maintain a neutral pH. The concentration used for samples containing only one peptide strand are 1.2 mM, determined by mass. For experiments including all three α chains, the peptides are mixed in a 1:1:1 ratio, with a total peptide concentration of 3.6 mM. Heterotrimer samples are annealed at 85° C. for 15 mM and then incubated for at least 72 h at room temperature before beginning the NMR measurements.

2.2.2. NMR Spectroscopy

All NMR experiments are recorded in an 800-MHz Varian spectrometer equipped with a cryogenic probe. The spectra are processed using the NMRpipe software (40) and analyzed using Sparky (41). Square cosine bell windows are used as apodization functions, and the data are zero-filled to the next power of 2 in both dimensions. Linear base-line corrections and forward-backward linear predictions are applied when necessary.

Monomeric samples are analyzed exclusively through two-dimensional total correlated spectroscopy (hereinafter "TOCSY[2]") at 25° C. In contrast, TOCSY and nuclear Overhauser effect spectroscopy (hereinafter "NOESY") experiments at 15 and 25° C. are recorded for the triple helical samples. $^1H,^{15}N$- and $^1H,^{13}C$-heteronuclear single quantum coherence experiments (HSQC) are recorded for the labeled samples at 25° C. To determine the register of the triple helix, a two-dimensional version of a four-dimensional $^1H,^{13}C$-HMQC-NOESY-$^1,H^{15}N$-HSQC experiment is recorded at 25° C. (42); hereinafter referred to as a two-dimensional $^{13}C,^{15}N$-edited NOESY. A three-dimensional HNHA experiment is also recorded at 25° C. to compute $^3J_{HNH\alpha}$ coupling constants (43). A three-dimensional HNHB experiment is also recorded at 25° C. to estimate the $^3J_{NH\beta}$ coupling constants (44). A qualitative approach is adopted in estimating the coupling constants and side chain rotamers (45).

2.2.3. Molecular Modeling

Homology models will be built starting from the crystal structure of a triple helical peptide (46). The necessary sequence changes are then made using PyMOL (47) to generate a preliminary structure for each of the six possible registers. Each structure will then be minimized using the AMBER99 (48) force field with implicit water (generalized Born approximation). Additional force field parameters to account for the stereo electronic effects of the hydroxyl group on the proline side chain conformation will included (49). Short constant temperature Langevin dynamics runs at 300, 200, and 100 K are used within the minimization algorithm to equilibrate the structures and obtain low energy conformers.

2.2.4. Conformational Restraints and Structure Calculation

Distance restraints are generated from the two-dimensional NOESY experiments. The peaks are mapped onto the shortest stretch of the chemical sequence that can unambiguously accommodate all inter- and intra-strand resonances. In adopting a qualitative approach, the peaks are divided into four categories (very strong, strong, medium, and weak) according to their intensity. The restraints are propagated along the sequence, assuming that all those amino acids have an identical conformation contributing equally to the observed peaks and leaving the N- and C-terminal triplets unconstrained because those amino acids have been shown to populate a less ordered conformation in homotrimeric triple helices (50).

Three types of dihedral restraints are used in the calculations. Because the Karplus equation generates up to four possible dihedral values for each coupling constant, a complementary strategy is used to obtain a single value to use in the refinement procedure. For example, in the case of glycine residues, this is straightforward, as each of the methylene protons affords a different coupling constant, one being shifted by a phase factor of 120°. Solving the equation using the coupling constant measured for each proton and comparing the solutions yields only one pair of angles that satisfies this condition. To obtain a value for aspartic acid and lysine, for example, a preliminary simulated annealing round starting from unfolded chains using distance restraints supplemented by dihedrals for all residues type except K and D, with coupling constants restraints for the charged residues (all possible solutions to the Karplus equation) is used. One can observe the low energy structures of the calculation and pick the solution of the Karplus equation that best agrees with the observed φ distribution for K and D residues.

Structure calculations are done using cycles of simulated annealing (SA) followed by a refinement in implicit solvent. In the SA stage, 300 trial structures will be calculated using a combination of torsional and Cartesian dynamics with the standard protocol available in the Crystallography and NMR System (CNS) software (51). The refinement stage is done in AMBER99, performing a minimization in implicit solvent subjected to the same constraints utilized in the SA stage on the 150 conformers that showed the lowest CNS target function. In the initial cycle, structure calculations start from extended polypeptide chains, and only backbone dihedral constraints are used. The minimum energy conformer is then be used to start a new cycle, in which only Cartesian dynamics will be used in the SA stage, but all the constraints available are included. The 15 conformers with the lowest energy, as calculated by AMBER, are then be selected for the final ensemble.

2.2.5. Results: Spin System Identification

The number of species present in the sample is determined from a nitrogen $^1H,^{15}N$-HSQC experiment using peptides with uniformly $^{15}N,^{13}C$-labeled amino acids. Some of the peaks can be identified as the monomeric forms of highly charged peptides using the information from TOCSY spectra of samples composed of each peptide separately. Other peptides readily form homotrimers in solution, and the presence of this species in the mixture will be identified using homonuclear spectra containing exclusively the peptide (50).

Most methylene groups present unique chemical shifts for both their diastereotopic protons with the exception of the γ-protons of proline and the δ- and ε-protons of lysine. Stereospecific assignments for the methylene groups with non-degenerate chemical shifts for the praline and hydroxyproline residues will be carried out using the NOE intensities of the cross-peaks between the β-, δ-, and α-protons and the β-, δ-, and γ-protons, respectively. Because of conformational restrictions placed on the methylene groups by the proline rings, these assignments will be straightforward. In the case of the α-protons of the glycine residues, a combination of NOE data and the cross-peak intensity in the HNHA spectrum will be used. A similar approach will taken for the β-protons of lysine and aspartic residues but using the information from the HNHB spectrum instead. The γ-protons of the lysine residues will be assigned exclusively based on NOE cross-peak intensity.

2.2.6. Results: Solution Structure

With knowledge of the register, the NOEs observed may be unambiguously assigned to proton pairs (or groups in the case of overlapping methylene resonances) along the chemical sequence of the peptides and, together with the constraints obtained from the HNHA and HNHB experiments, used to calculate an a ensemble of structures that will be representative of the solution conformation of the triple helix. Such results allow for assignment of the stagger determining capacity of the NC2 Domain.

2.3. Crystallization and Structure Determination of the NC2 Domain of Type IX Collagen

2.3.1. Peptide Sequences

The peptide employed in the instant crystallization experiment are synthesized on an ABI433A peptide synthesizer with 0.25 mM Fmoc-Gly-PEG-PS resin, a 4-fold excess of Fmoc amino acids and O-(7-azabenzotriazol-1-yl)-N,N,N', N'-tetramethyluronium hexafluoro-phosphate as activating agent. The Fmoc amino acids carry the appropriate protecting groups. The peptides are cleaved off the resin and deprotected for 4 h at room temperature with 90% trifluoroacetic acid, 5% thioanisole, 3% 1,2-ethanedithiol, 2% anisole. Subsequently, the peptide is precipitated in cold ether, redissolved in H2O, and lyophilized. The reduced peptide is then purified by reverse phase HPLC using a $C_{18}$ column (Vydac, Hesperia, Calif.; 50×250 mm, 10-15-µm particle size, 300-Å pores) with an acetonitrile/water gradient and 0.1% trifluoroacetic acid as an ion-pairing agent. Finally, the peptide is characterized by electrospray/quadrupole/time-of-flight mass spectrometry (Q-tofinicro; Waters Associates) and amino acid analysis.

2.3.3. Peptide Folding, Oxidation, and Purification of Disulfide-Linked Trimer The lyophilized, reduced peptide is dissolved in degassed and $N_2$ saturated 50 mM sodium acetate buffer, pH 4.5, under an $N_2$ atmosphere and kept at 4° C. for 24 h to allow triple helix formation prior to oxidation. Two strategies of oxidation may be used: exposure to atmospheric $O_2$ or addition of reduced (10 mM) and oxidized (1 mM) glutathione and exposure to atmospheric $O_2$. In both cases, the pH will be raised to 8.3 with a saturated solution of Tris. Oxidation is carried out for 5-7 days, and the peptide mass is periodically analyzed by liquid chromatography-mass spectrometry. To separate covalently linked trimeric peptide from other oligomers, the oxidized crude material is dissolved in a deionized 8M urea solution with 0.1% trifluoroacetic acid to prevent disulfide exchange, and applied to a sieve column. Trimer-containing fractions are pooled out and further purified by reverse phase HPLC using a $C_{18}$ column.

2.3.4. Peptide Crystallization, Data Collection, Structure Determination, and Refinement The purified and lyophilized covalently linked trimeric collagen IX peptide is then dissolved at a concentration of 15 mg/ml in 5 mM acetic acid. The peptide is crystallized at 22° C. using the hanging drop vapor diffusion method. For crystallization, 2 µl of the peptide solution is mixed with 2 µl of the reservoir solution of 20% polyethylene glycol monomethyl ether. Several strategies for cryoprotection can be tried in an attempt to improve the quality of the diffraction. The data will then be collected at ALS Beamline 8.2.1. For data collection, glycerol is first added to the drop containing the crystal for a final concentration of 10%. The drop will sit for 8 h, and the crystal will be placed directly in the cryostream. If, at this point the mosaic spread is still unacceptably high, the crystal is then annealed several times by removing the crystal from the cryostream and placing it back in the drop solution. After further annealing cycles the diffraction may be of sufficient quality to collect data. A complete three wavelength MAD data set is then collected on the crystal and used for structure determination. The positions of selenomethionines in the triple helix is obtained using SOLVE. The phases obtained from these positions will be improved by density modification in CNS, and the resulting density modified map will be used for model building (51, 52, 53). After two-thirds of the structure is built, phase combination using phases from the partial model will be used to improve the map. This penults the a structure of one complete triple helix in the crystallographic asymmetric unit (ASU) to be built.

2.3.5. Analysis of Triple Helix Geometry

Helical parameters will be calculated based on the method of Sugeta and Miyazawa (55) for every amino acid residue using the program, PHEL (56). The input data for the calculation of the jth triplet will consist of three sets of nine parameters for the jth, (f+1)th, and (j+2)th amino acid residues. Nine parameters of the jth amino acid residue are bond lengths of N(j)-C'(j), C'(j)-C'(j), and C'(j)-N(j+1), bond angles of C'(j−1)-N(j)-Cα(j), N(j)-Cα(j)-C'(j) and Cα(j)–C' (j)-N(j+1), and dihedral angles of C'(j−1)-N(j)–Cα(j)–C'(j), N(j)–Cα(j)–C'(j)-N(j+1), and Cα(j)–C'(j)-N(j+1)–Cα(j+1). Such analysis allows for assignment of the stagger determining capacity of the NC2 Domain.

The contents of all figures and all references, patents, and published patent applications cited throughout this application are expressly incorporated herein by reference.

REFERENCES

1. Myllyharju, J. & Kivirikko, K. I. (2004) Trends Genet. 20, 33-43.
2. Ricard-Blum, S. & Ruggiero, F. (2005) Pathol. Biol. 53, 430-442.
3. Mazzorana, M., Gruffat, H., Sergeant, A. & van der Rest, M. (1993) J. Biol. Chem. 268, 3029-3032.
4. Lesage, A., Penin, F., Geourjon, C., Marion, D. & van der Rest, M. (1996) Biochemistry 35, 9647-9660.
5. Mazzorana, M., Cogne, S., Goldschmidt, D. & Aubert-Foucher, E. (2001) J. Biol. Chem. 276, 27989-27998.
6. Boudko, S. P., Engel, J. & Bachinger, H. P. (2008) J. Biol. Chem. 283, 34345-34351.
7. McAlinden, A., Smith, T. A., Sandell, L. J., Ficheux, D., Parry, D. A. D. & Hulmes, D. J. S. (2003) J. Biol. Chem. 278, 42200-42207.
8. Eyre, D. R. & Wu, J. J. (1995) J Rheumatol Suppl 43, 82-85.
9. Fässler, R., Schnegelsberg, P. N., Dausman, J., Shinya, T., Muragaki, Y., McCarthy, M. T. Olsen, B. R. & Jaenisch, R. (1994) Proc. Natl. Acad. Sci. U.S.A. 91, 5070-5074.
10. Diab, M. (1993) Orthop Rev 22, 165-170.
11. Asamura, K., Abe, S., Imamura, Y., Aszodi, A., Suzuki, N., Hashimoto, S., Takumi, Y., Hayashi, T., Fässler, R., Nakamura, Y. & Usami, S. (2005) Neuroscience 132, 493-500.
12. Boyd, L. M., Richardson, W. J., Allen, K. D., Flahiff, C., Jing, L., Li, Y., Chen, J. & Setton, L. A. (2008) Arthritis Rheum. 58, 164-171.
13. Carter, E. M. & Raggio, C. L. (2009) Curr. Opin. Pediatr. 21, 46-54.
14. Labourdette, L. & van der Rest, M. (1993) FEBS Lett. 320, 211-214.
15. Mechling, D. E., Gambee, J. E., Morris, N. P., Sakai, L. Y., Keene, D. R., Mayne, R. & Bächinger, H. P. (1996) J. Biol. Chem. 271, 13781-13785.
16. Jäälinoja, J., Ylöstalo, J., Beckett, W., Hulmes, D. J. S. & Ala-Kokko, L. (2008) Biochem. J. 409, 545-554.

17. Wu, J. J., Lark, M. W., Chun, L. E. & Eyre, D. R. (1991) J. Biol. Chem. 266, 5625-5628.
18. Kammerer, R. A., Schulthess, T., Landwehr, R., Lustig, A., Fischer, D. & Engel, J. (1998) J. Biol. Chem. 273, 10602-10608.
19. Boudko, S. P., Engel, J., Okuyama, K., Mizuno, K., Bächinger, H. P. & Schumacher, M. A. (2008) J. Biol. Chem. 283, 32580-32589.
20. Boudko, S. P. & Engel, J. (2004) J. Mol. Biol. 335, 1289-1297.
21. Pihlajamaa, T., Perälä, M., Vuoristo, M. M., Nokelainen, M., Bodo, M., Schulthess, T., Vuorio, E., Timpl, R., Engel, J. & Ala-Kokko, L. (1999) J. Biol. Chem. 274, 22464-22468.
22. Bruckner, P., Mendler, M., Steinmann, B., Huber, S. & Winterhalter, K. H. (1988) J. Biol. Chem. 263, 16911-16917.
23. Paassilta, P., Pihlajamaa, T., Annunen, S., Brewton, R. G., Wood, B. M., Johnson, C. C., Liu, J., Gong, Y., Warman, M. L., Prockop, D. J., Mayne, R. & Ala-Kokko, L. (1999) J. Biol. Chem. 274, 22469-22475.
24. Okada, Y., Konomi, H., Yada, T., Kimata, K. & Nagase, H. (1989) FEBS Lett. 244, 473-476.
25. Burrage, P. S., Mix, K. S. & Brinckerhoff, C. E. (2006) Front. Biosci. 11, 529-543.
26. Vaughan, L., Mendler, M., Huber, S., Bruckner, P., Winterhalter, K. H., Irwin, M. I. & Mayne, R. (1988) J. Cell Biol. 106, 991-997.
27. van der Rest, M. & Mayne, R. (1988) J. Biol. Chem. 263, 1615-1618.
28. Rowley, M. J., Nandakumar, K. S. & Holmdahl, R. (2008) Mod Rheumatol 18, 429-441.
29. Jäälinoja, J., Nissilä, M., Kauppi, M. J., Hakala, M., Laiho, K., Karttunen, R., Hörkkä, S. & Ala-Kokko, L. (2008) J. Rheumatol. 35, 745-751.
30. Hedbom, E., Antonsson, P., Hjerpe, A., Aeschlimann, D., Paulsson, M., Rosa-Pimentel, E., Sommarin, Y., Wendel, M., Oldberg, A. & Heinegård, D. (1992) J. Biol. Chem. 267, 6132-6136.
31. DiCesare, P., Hauser, N., Lehman, D., Pasumarti, S. & Paulsson, M. (1994) FEBS Lett. 354, 237-240.
32. Mörgelin, M., Heinegård, D., Engel, J. & Paulsson, M. (1994) Biophys. Chem. 50, 113-128.
33. Rosenberg, K., Olsson, H., Mörgelin, M. & Heinegård, D. (1998) J. Biol. Chem. 273, 20397-20403.
34. Holden, P., Meadows, R. S., Chapman, K. L., Grant, M. E., Kadler, K. E. & Briggs, M. D. (2001) J. Biol. Chem. 276, 6046-6055.
35. Thur, J., Rosenberg, K., Nitsche, D. P., Pihlajamaa, T., Ala-Kokko, L., Heinegård, D., Paulsson, M. & Maurer, P. (2001) J. Biol. Chem. 276, 6083-6092.
36. Munakata, H., Takagaki, K., Majima, M. & Endo, M. (1999) Glycobiology 9, 1023-1027.
37. Pihlajamaa, T., Lankinen, H., Ylöstalo, J., Valmu, L., Jäälinoja, J., Zaucke, F., Spitznagel, L., Gösling, S., Puustinen, A., Mörgelin, M., Perämen, J., Maurer, P., Ala-Kokko, L. & Kilpeläinen, I. (2004) J. Biol. Chem. 279, 24265-24273.
38. Leppänen, V., Tossavainen, H., Permi, P., Lehtiö, L., Rönnholm, G., Goldman, A., Kilpeläinen, I. & Pihlajamaa, T. (2007) J. Biol. Chem. 282, 23219-23230.
39. Fresquet, M., Jowitt, T. A., Ylöstalo, J., Coffey, P., Meadows, R. S., Ala-Kokko, L., Thornton, D. J. & Briggs, M. D. (2007) J. Biol. Chem. 282, 34634-34643.
40. Delaglio, F., Grzesiek, S., Vuister, G. W., Zhu, G., Pfeifer, J., and Bax, A. (1995) J. Biomol. NMR 6, 277-293.
41. Goddard, T. D., and Kneller, D. G. (2008) SPARKY 3, Version 3.115 University of California, San Francisco, Calif.) and ccpnmr (Vranken, W. F., Boucher, W., Stevens, T. J., Fogh, R. H., Pajon, A., Llinas, M., Ulrich, E. L., Markley, J. L., Ionides, J., and Laue, E. D. (2005) Proteins 59, 687-696.
42. Muhandiram, D. R., Guang, Y. X., and Kay, L. E. (1993) J. Biomol. NMR, 13, 463-470.
43. Vuister, G. W., and Bax, A. (1993) J. Am. Chem. Soc. 115, 7772-7777.
44. Archer, S. J., Ikura, M., Torchia, D. A., and Bax, A. (1991) J. Magn. Reson. 95, 636-641.
45. Powers, R., Garrett, D. S., March, C. J., Frieden, E. A., Gronenbom, A. M., and Clore, G. M. (1993) Biochemistry 32, 6744-6762.
46. Berisio, R., Vitagliano, L., Mazzarella, L., and Zagari, A. (2002) Protein Sci. 11, 262-270.
47. Delano, W. L. (2002) The PyMOL Molecular Graphics System, Delano Scientific, San Carlos, Calif.
48. Case, D. A., Cheatham, T. E., 3rd, Darden, T., Gohlke, H., Luc, R., Merz, K. M., Jr., Onufriev, A., Simmerling, C., Wang, B., and Woods, R. J (2005) J. Comput. Chem. 26, 1668-1688.
49. Park, S., Radmer, R. J., Klein, T. E., and Pande, V. S. (2005) J. Comput. Chem. 26, 1612-1616.
50. Li, M. H., Fan, P., Brodsky, B., and Baum, J. (1993) Biochemistry 32, 7377-7387.
51. Brünger, A. T., Adams, P. D., Clore, G. M., DeLano, W. L., Gros, P., Grosse-Kunstleve, R. W., Jiang, J. S., Kuszewski, J., Nilges, M., Pannu, N. S., Read, R. J., Rice, L. M., Simonson, T., and Warren, G. L. (1998) Acta Crystallogr. D Biol. Crystallogr. 54, 905-921.
52. Terwilliger, T. C., and Berendzen, J. (1999) Acta Crystallogr. Sect. D Biol. Crystallogr. 55, 849-861.
53. Jones, T. A., Zou, J. Y., Cowan, S. W., and Kjeldgaard (1991) Acta Crystallogr. Sect. A 47, 110-119.
54. Laskowski, R. A., MacArthur, M. W., Moss, D. S., and Thornton, J. M. (1993) J. Appl. Crystallogr. 26, 283-291.
55. Sugeta, H., and Miyazawa, T. (1967) Biopolymers 5, 673-679.
56. Okuyama, K., Wu, G., Jiravanichanun, N., Hongo, C., and Noguchi, K. (2006) *Biopolymers* 84, 421-432.

What is claimed is:

1. A Collagen IX NC2 domain-conjugate composition comprising a heterologous moiety operably linked to a Collagen IX NC2 domain consisting of the peptide sequence of SEQ ID 19, SEQ ID 20, or SEQ ID 21.

2. The composition of claim 1 further comprising two additional Collagen IX NC2 domain-conjugates, whereby the three Collagen IX NC2 domain-conjugates comprise a trimer.

3. The composition of claim 2, wherein the trimer is a heterotrimer.

4. The composition of claim 3, wherein the first Collagen IX NC2 domain of the trimer consists of the peptide sequence of SEQ ID 19, the second Collagen IX NC2 domain-consists of the peptide sequence of SEQ ID 20, and the third Collagen IX NC2 domain consists of the peptide sequence of SEQ ID 21.

5. The composition of claim 1 wherein the heterologous moiety is selected from the group consisting of: a diagnostic agent; a therapeutic agent; a targeting agent; and a labeling agent.

6. The composition of claim 5 wherein the heterologous moiety is a therapeutic agent selected from the group consisting of: a chemotherapeutic agent; a radioisotope; an anti-angiogenic agent; a cytokine; a chemokine; a growth factor; an enzyme; an immunomodulator; a hormone; and a toxin.

7. The composition of claim 5 wherein the heterologous moiety is a labeling agent selected from the group consisting of: a photodetectable label; a contrast agent; a paramagnetic label; an ultrasound label; and a nanoparticle.

8. The composition of claim 1 herein the heterologous moiety is operably linked to the amino terminus of the Collagen IX NC2 domain.

9. The composition of claim 8 comprising a heterologous moiety operably linked to the carboxy terminus of the Collagen IX NC2 domain.

10. The composition of claim 1 herein the heterologous moiety is operably linked to the carboxy terminus of the Collagen IX NC2 domain.

11. The composition of claim 10 comprising a heterologous moiety operably linked to the amino terminus of the Collagen IX NC2 domain.

* * * * *